(12) United States Patent
Zhou

(10) Patent No.: US 7,749,367 B2
(45) Date of Patent: Jul. 6, 2010

(54) VERTICAL SLAB GEL ELECTROPHORESIS CELL AND METHOD THEREFOR

(76) Inventor: Deming Zhou, 310 Brookwood Dr., Richardson, TX (US) 75080

( * ) Notice: Subject to any disclaimer, the term of this patent is extended or adjusted under 35 U.S.C. 154(b) by 802 days.

(21) Appl. No.: 10/382,159

(22) Filed: Mar. 5, 2003

(65) Prior Publication Data

US 2004/0195103 A1    Oct. 7, 2004

(51) Int. Cl.
*G01N 27/453*    (2006.01)
(52) U.S. Cl. .............. 204/467; 204/615; 204/618; 204/619; 204/621
(58) Field of Classification Search ................ 204/456, 204/466, 467, 606, 616, 618, 615, 619, 621
See application file for complete search history.

(56) References Cited

U.S. PATENT DOCUMENTS

| | | | | |
|---|---|---|---|---|
| 3,932,265 A | * | 1/1976 | Hoefer | 204/619 |
| 4,560,459 A | * | 12/1985 | Hoefer | 204/467 |
| 5,186,807 A | * | 2/1993 | Sanford et al. | 204/618 |
| 5,188,790 A | * | 2/1993 | Magnant | 264/219 |
| 5,538,614 A | * | 7/1996 | Han | 204/613 |
| 5,632,877 A | * | 5/1997 | Van Atta | 204/618 |
| 6,001,233 A | * | 12/1999 | Levy | 204/618 |
| 6,193,868 B1 | * | 2/2001 | Hsu | 204/618 |
| 6,398,933 B1 | * | 6/2002 | Scott | 204/466 |
| 6,436,262 B1 | * | 8/2002 | Perez | 204/618 |

* cited by examiner

Primary Examiner—Kaj K Olsen

(57) ABSTRACT

In the present vertical slab-gel electrophoresis instrument, all the vertical slab gel cassettes comprise un-notched rectangular sidewalls and flanged spacer strips, but still can form a U-notched upper opening with an even rim for each cassette; one type of cassette can undergo gel casting with an electrophoresis cell, while another two types of cassettes can be used to form a multiple-cassette electrophoresis cell. The present invention can also incorporate a swing-frame chosen for urging a cassette to join an upper buffer chamber, provides an improved cooling device such that there is no need for the use of exogenous coolant, and also provides simple methods to enable cassettes to be tightly enclosed within membrane pouches for gel casting.

16 Claims, 13 Drawing Sheets

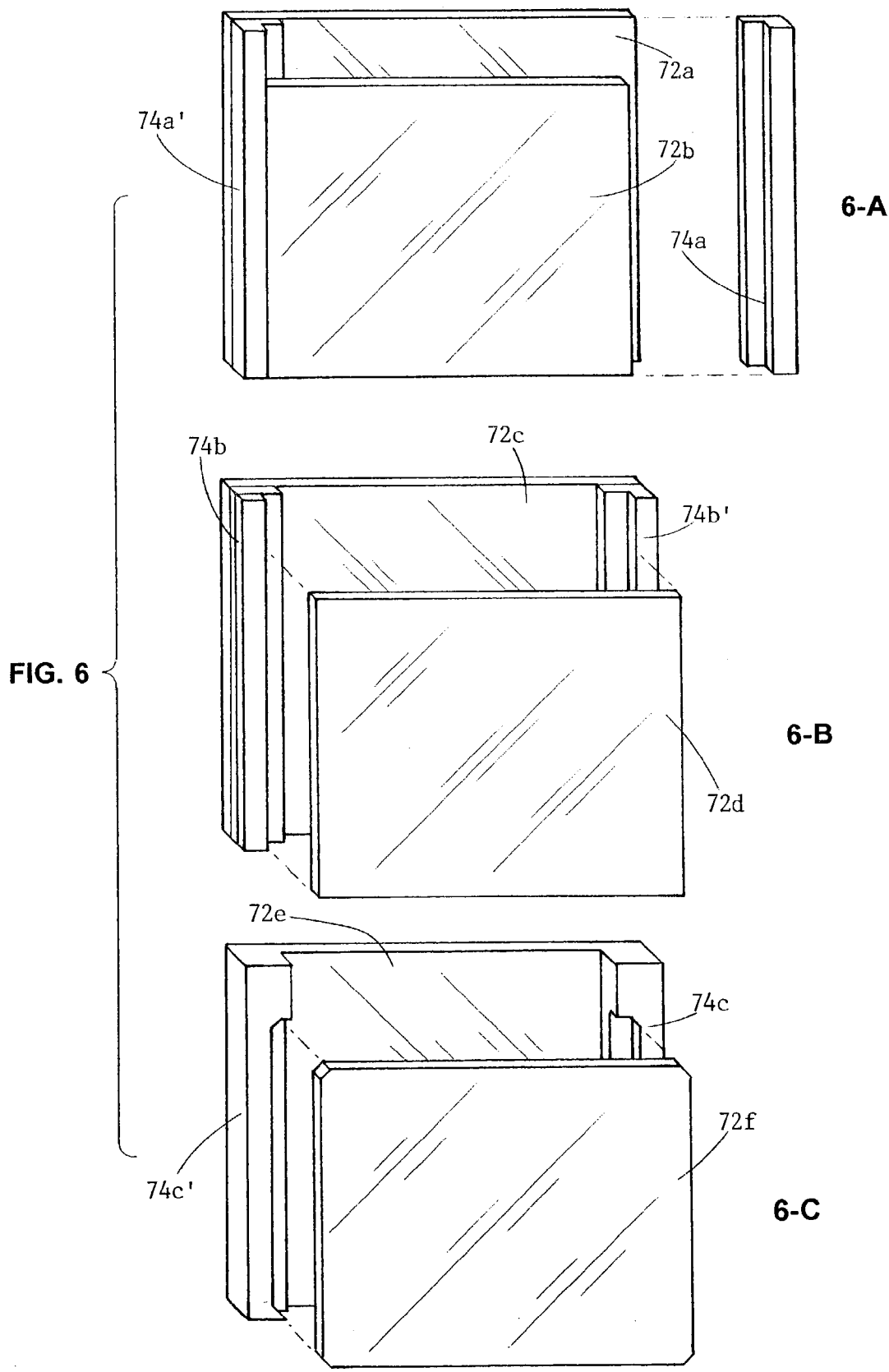

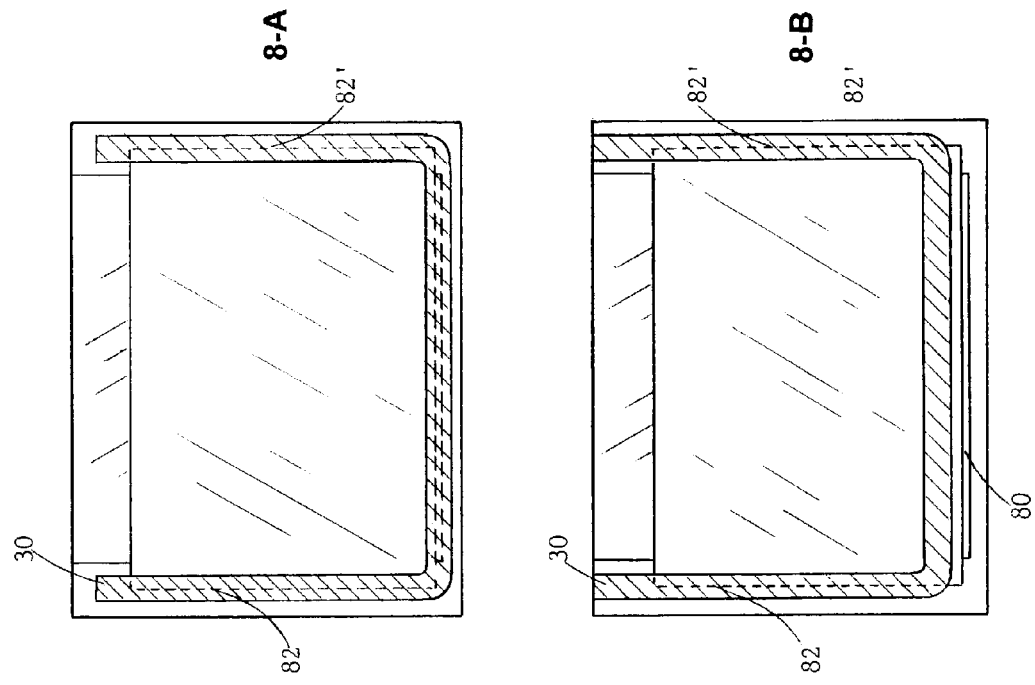
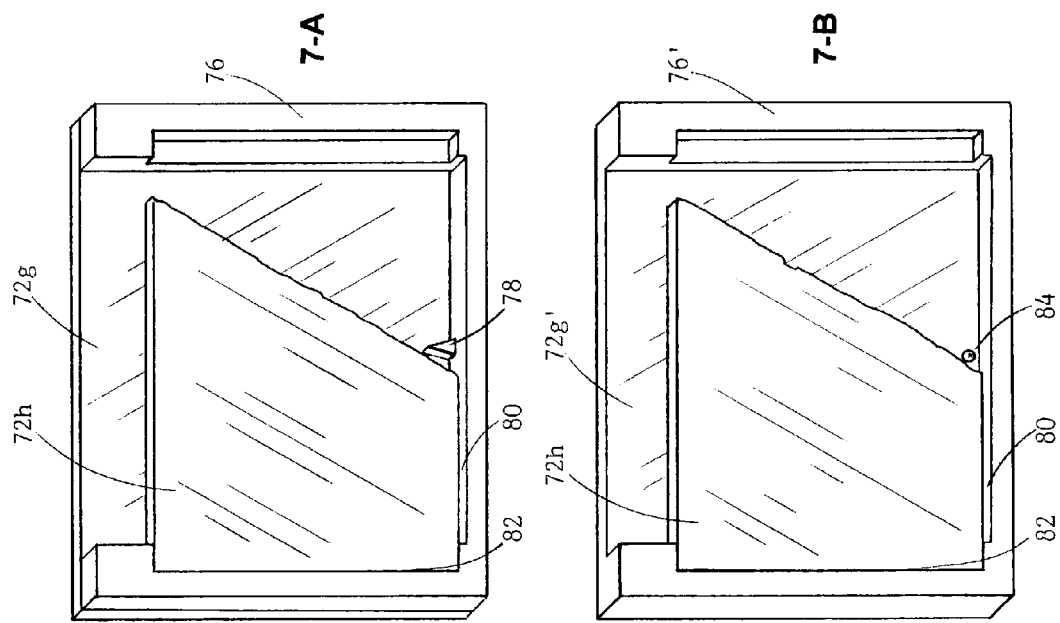
FIG. 8
FIG. 7

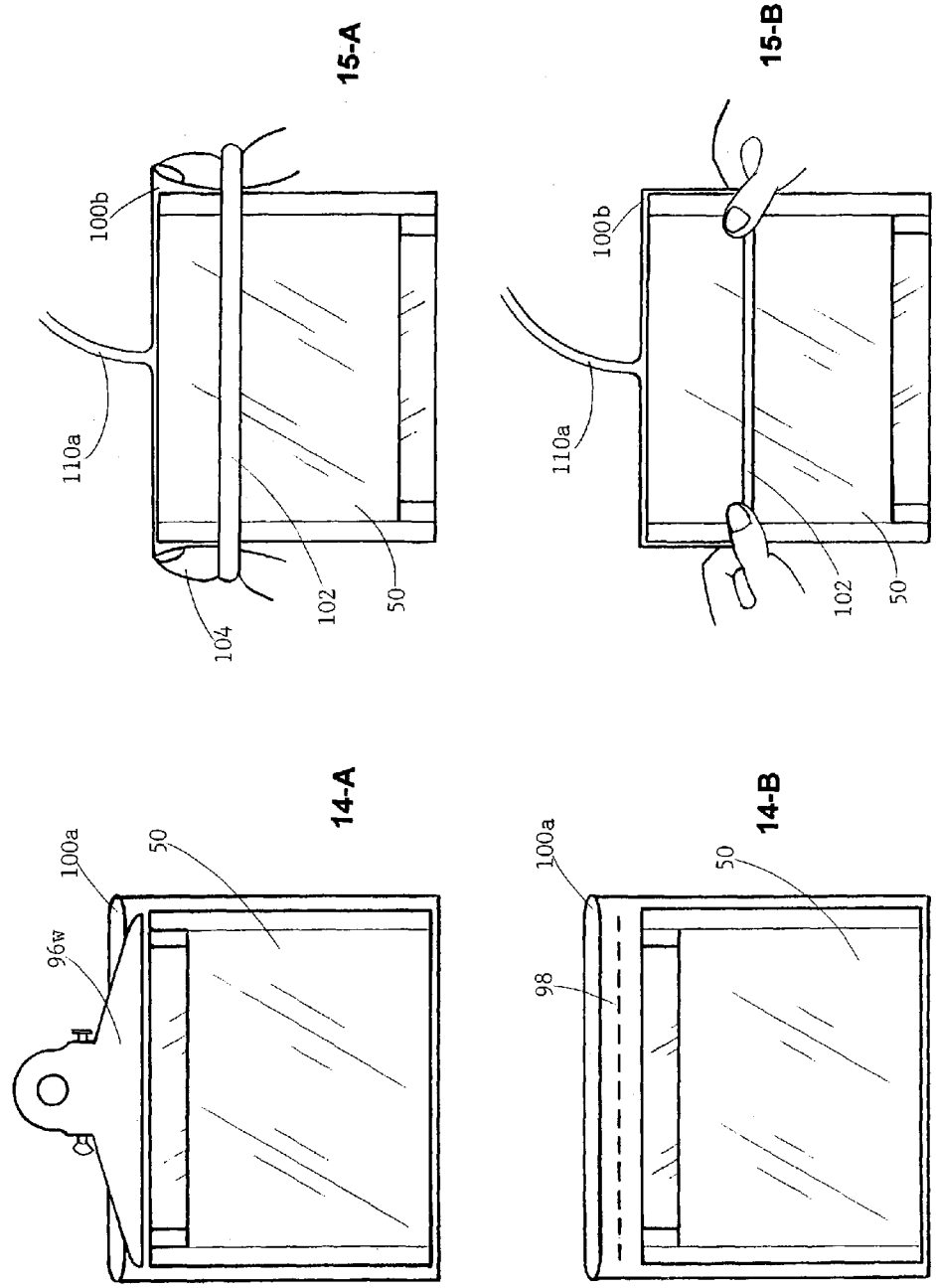

VERTICAL SLAB GEL ELECTROPHORESIS CELL AND METHOD THEREFOR

BACKGROUND

1. Field of Invention

This invention relates to electrophoresis equipment and method, and specifically to improved vertical slab gel electrophoresis equipment and related methods.

2. Prior Art and Comment

Ferdinand Ruess, a Russian physicist, watched the migration of clay colloidal particles between two electrodes in 1897. About 50 years later, Arne Tiselius, a Swedish chemist, studied the migration of protein molecules in electric field, demonstrated the complex nature of serum proteins by using a prototype that he termed as a free electrophoresis apparatus. Whereby he won the Nobel Prize for chemistry of 1948. Electrophoresis has now become a versatile and powerful technique in biomedical and related research areas. It can be employed to fractionalize almost any charged particle, from ionizable small molecules to whole cells. When an electrophoresis carries out in a gel matrix, it terms as gel electrophoresis. Gel electrophoresis has very high resolution, is mainly employed to fractionate biomacromolecular species, such as DNA, RNA or proteins. That is because the network of the gel matrix acts as a molecular sieve to retard the migration of the macromolecular species according to their size and shape. Besides, the gel matrix can also stabilize the boundaries of the separated species both during and after the electrophoresis, so as to facilitate the subsequent analyses. The widely employed gel matrixes are agarose gel and polyacrylamide gel. The latter can be cast into a vertical cavity due to it can adhere better to the cavity walls. By successfully exploited the high fractionation ability of vertical slab polyacrylamide gel electrophoresis for determination the base sequences of DNA, Frederick Sanger, a British biochemist, and his American colleague Walter Gilbert were awarded the Nobel Prize for chemistry of 1980.

In vertical slab gel electrophoresis (abbreviated as VSGE hereafter), the electrophoretic vector travels vertically within a slab shaped gel matrix uprightly arranged between an upper and a lower pH buffer solution chambers charged with opposite electrodes. Usually the gel slab is only 0.2 to 2.0 mm in thickness. None such a gel slab can stand uprightly by itself unless it is held in a cassette; none such a gel slab can be properly held in a cassette unless it is directly cast and formed in it. Therefore, and obviously, there are three basic problems regarding the design of any VSGE cell: (i) how to construct a vertical slab gel casting cassette (abbreviated as VSGC cassette, gel casting cassette, or cassette hereafter) having sealed left and right edges but opened up and low ends; (ii) how to insure a gel matrix to be cast into the cassette without leakage; and (iii) how to urge the cassette to water-tightly join the upper buffer chamber (abbreviated as UBC hereafter) with the upper opening of the cassette exposes into the formed cassette/UBC complex. As long as the cassette/UBC complex forms, just sets it into a lower buffer chamber (abbreviated as LBC thereafter), thereupon a VSGE cell is accomplished. As for how to arrange the electrodes in the UBC and LBC, and how to make a lid for the VSGE cell, those are foolproof.

About the size: Typically there were three different sized VSGE cells. The 36×30 cm slab gels were usually used for DNA sequencing electrophoresis. But it has been replaced by some automatic capillary gel electrophoresis instruments in the developed countries, referring to U.S. Pat. No. 5,374,527 (1994), etc. The 18×16 cm slab gels were widely used for protein fractionation in the early years. However nowadays, more than 95% chance is to run the mini gel, which casts in 8×10, or 10×10 cm cassettes, due to its shorter running time and easer to manipulate.

About the structure style: There were several different styled VSGE cells, referring to U.S. Pat. No. 3,719,580 (1973), U.S. Pat. No. 4,224,134 (1980) and U.S. Pat. No. 4,574,040 (1986), etc. However, the most popular styled VSGE cell is a kind of dual gel cell, which was initiated by Madjar et al (1) in 1977. Thereafter various VSGE cells were patented, but most of them wore still belong to the most popular styled dual gel cell as mentioned above, referring to U.S. Pat. No. 4,574,040 (1986), U.S. Pat. No. 5,632,877 (1997), U.S. Pat. Nos. 5,888,369 and 6,001,233 (1999), etc. Their common structure style is that; on one hand, making the UBC to have two opposite U-shaped side openings; on the other hand, making each cassette to have a U-notched upper opening; and then using an urging mechanism to force those two cassettes to sandwich that UBC between them. Certainly, U-shaped rubber sealing-gaskets are always employed for sealing up the interfaces between the cassettes and UBC. As a result, a water-tightly joined cassettes/UBC complex is formed with the two U-notched upper openings naturally expose into the formed complex. However, their common weakness is that when only one gel runs in such a dual gel cell, the other side opening of the UBC has to be blocked up. It is inconvenient, because more than 50% chance is to run one gel a time. In CN Pat. 88106198.0 (1982), the inventor developed a modular VSGE cell, which allows numerous slab gels to run in it parallel.

About the cassette: compare with any kind plastic, glass plate is a better material to wall VSGC cassettes, due to it has much higher rigidity, much higher chemical inertness, much higher thermal conductivity; and especially due to the gel matrix can adhere it better. Ceramic, such as aluminum oxide plate, is even better than glass, but it is not transparent and cannot be as cheap as glass plate. Unfavorably, both of them are typical bad machining-able materials, so that to make glass and/or ceramic walled cassettes can never be as easy as to make them by plastics. Nevertheless, any reusable cassette is had better to be glass and/or ceramic walled by the reason as mentioned above. The simplest glass walled cassettes was formed by two identical rectangular glass plates and a pair of flat plastic spacer strip, as reported by Herbert Tichy (2) in 1966. However, this kind cassette is not easy to join the UBC, and its sample loading area is not easy to access, referring to U.S. Pat. No. 4,224,134 (1980). Afterward, one of the two rectangular glass plates was replaced by a U-notched glass plate, so as to make the cassette having a U-notched upper opening, referring to the report of F. W. Studier (3) in 1973. However, the U-notched glass or ceramic plates are much more costly and much more fragile than rectangular plates. Subsequently, the U-notched glass wall was replaced back by a shorter rectangular glass wall, as in U.S. Pat. No. 4,574,040. Although the shorter glass wall along with two flat plastic spacer strips also can form a U-notched upper opening for the cassette, but this way formed U-notched upper opening does not have an even rim. As a result, the leakage of the upper pH buffer solution becomes the major problem if this kind cassette is employed in any VSGE cell, referring to the Tech Note (4). Cross section T-shaped spacer strips were used to form a cassette in U.S. Pat. No. 4,560,459 (1985), but that cassette still had to use a U-notched sidewall. A three-element cassette was disclosed in U.S. Pat. No. 4,954,236 (1990), but its abutting face has no even margin to insure a leak-free abutting.

Besides, a fact was examined in the prior art. That is under appropriate pressure, the left and right margins of those glass walled VSGE cassettes could achieve leak-free, provided the employed two plastic spacer strips are wide and smooth enough, therefore makes no need using grease or glue to seal up the left and right margins.

About the urging mechanism: An urging mechanism is always required for forcing the cassette and the UBC to rest on each other tightly. Most employed urging mechanisms were too complex and lax, so that large LBC were always required, refereeing to U.S. Pat. No. 4,574,040 (1986), U.S. Pat. No. 5,632,877 (1997) and U.S. Pat. Nos. 5,888,369, 6,001,233 (1999), etc. A compact clamp urging mechanism was disclosed recently in U.S. Pat. No. 6,436,262 (2002), but it looks short of compatibility.

About the gel casting: Essentially the process of gel casting is same to the process of the Plexiglas plate manufacturing, as disclosed in U.S. Pat. No. 2,154,639 (1939) of Rohm et al. However, herein the formed polymer is a hydrophilic gel matrix, is not supposed to be moved out off the mold for any other use, but is for stay in situ as a matrix for an electrophoresis to take place therein. Most ordinary VSGC cassettes can be arranged in face to face, put into a gel-casting box to perform gel casting. The first gel casting box, and the method of gradient slab gel casting was reported by Margolis et al (5) in 1968. Different size, different improved gel casting boxes are commercially available nowadays. However, their common defect is lacking of flexibility. G. P. Magnant patented a casting method for forming a gel matrix in U.S. Pat. No. 5,188,790 (1993). However since several thousand years ago, our human being already knew how to form objects by casting. The chemical mechanism of the polyacrylamide gel formation for electrophoresis was published by Leonard Ornstein (6) in 1964. Of course, any kind of casting needs a mold. If Magnant patented apparatuses is a three-element assembled mold, it had been disclosed by Rohm et al 54 years ago before him. Even though, the problem is how to carry out an electrophoresis in such a three-element mold, which has no lower opening. Overlooking of all other problems, and if there is no misunderstood to us, then the patented method of Magnate seems nothing more than putting a ordinary cassette into a ordinary loose plastic membrane bag, and then using four objects from four sides to push the loose bag towards the cassette for gel casting. If so, Magnant patented method looks neither convenient nor flexible than using those gel casting boxes. Several different methods were designed to seal up the lower openings of VSGC cassettes for gel casting, referring to U.S. Pat. No. 4,224,134 (1980), U.S. Pat. No. 5,192,408 (1993), U.S. Pat. No. 5,520,790 (1996), U.S. Pat. Nos. 6,110,340 and 6,162,342 (2000), etc. But most of them have no compatibility, some are not dependable, some are inconvenient.

About the heat absorbing device: Joule-heating generates in the gel matrix during electrophoresis. A heat-absorbing device is required in a VSGE cell when the samples need to run in native state. However in most cases, such as in DNA sequencing gel electrophoresis or SDS protein gel electrophoresis, the samples need to run in denatured state, therefore making no heat-absorbing device is required. All heat-absorbing devices in the prior art need to use exogenous coolant, referring to U.S. Pat. No. 4,224,134 (1980) and U.S. Pat. No. 4,574,040 (1986), etc.

SUMMARY

According to the present innovates, almost all aspects of VSGE cell and the related method have been improved; wherein 6 embodiments embodied 3 different mechanisms for urging the cassette to abut to the UBC, each of them has its merit; a dual gel cell allows not to block up the other side opening when a single gel runs in it; all cassettes are formed by rectangular sidewalls and fringed spacer strips, but still can form a U-notched upper opening with even rim for every cassette; two kind cassettes can undergo the gel casting within the VSGE cell, other two kind cassettes can form an unlimited cassette/UBC complex, which is ideal for the 2-D electrophoresis; a cooling device needs not exogenous coolant; improved rubber sealing-gasket has higher elasticity and higher compatibility to thickness different cassettes; disclosed four convenient methods can snugly encase almost all kind cassettes into membrane pouch for performing homogeneous or gradient gel casting.

OBJECTS AND ADVANTAGES

Accordingly, the objects and advantages of the present invention are:

(a) planting a septum wall or a cooling chamber into a UBC, raising up the altitude of the electrodes in it, and using a shallower LBC, so as to allow unnecessary blocking up the other side opening when a single gel runs in such a dual gel cell;

(b) equipping a swing-frame aside each U-shaped side opening of the UBC; swung-open it allowing a cassette to insert therebetween; swing-close it can urge the cassette to abut the UBC tightly; this mechanism is novel, compact, flexible and easy to operate;

(c) arranging a UBC along with two cassettes into a right angle trapezoidal apron, thus a V-shaped gap is formed therebetween; to push a cylinder-beam into the V-shaped gap can urge the cassette(s) to abut the UBC tightly; this mechanism is also novel, compact, flexible and easy to operate;

(d) holding a cam-beam aside a cassette, which faces a U-shaped side opening of the UBC; turn-close the cam-beam also can urge the cassette to abut the UBC tightly; this mechanism his nothing to do with the LBC;

(e) persisting in using glass and/or ceramic plates to wall the VSGC cassettes, so as to make the formed cassettes has higher rigidity, better heat dissipation, and allows the gel matrix to adhere better to the cassette walls;

(f) using non-notched side walls and flanged spacer strips to form all cassettes, but still can form a U-notched upper opening with even rim for every cassette, so as to insure a leak-free abutting to the UBC, and can significantly reduce the cost and the fragility of the cassettes;

(g) two kind cassettes can undergo the gel casting within the VSGE cell, so that nothing else is required;

(h) other two kind cassettes can form an infinite cassette/UBC complex, which is ideal for the 2-D electrophoresis running;

(i) improved rubber sealing gasket has an 8-shaped cross section, so as to have much higher compressibility and elasticity, to be compatible with thickness different cassettes;

(j) an improved heat-absorbing device does not need exogenous coolant, so that is very convenient to use; and (k) four disclosed convenient methods can snugly encase almost all kind VSGC cassettes into membrane pouches for both homogeneous and the gradient gel casting without leakage.

BRIEF DESCRIPTION OF THE DRAWINGS

FIG. 6 is a set of exploded perspective view showing the structure of the improved VSGC cassettes 6-A, 6-B and 6-C.

FIG. 7 is a set of fragmentary perspective view showing the structure of the improved VSGC cassette 7-A and 7-B.

FIG. 8 is a set of front view showing the position relationship of the U-shaped rubber sealing-gasket versus the cassette 7-A or 7-B during gel casting or electrophoresis running respectively.

FIG. 14 is a set of front view showing a method for snugly encasing the VSGC cassettes into a lower softening point plastic membrane pouch for gel casting.

FIG. 15 is a set of front view showing a method for snugly encasing the VSGC cassettes into an elastic membrane pouch for gel casting.

DESCRIPTION OF THE PREFERRED EMBODIMENTS

Figure 1:
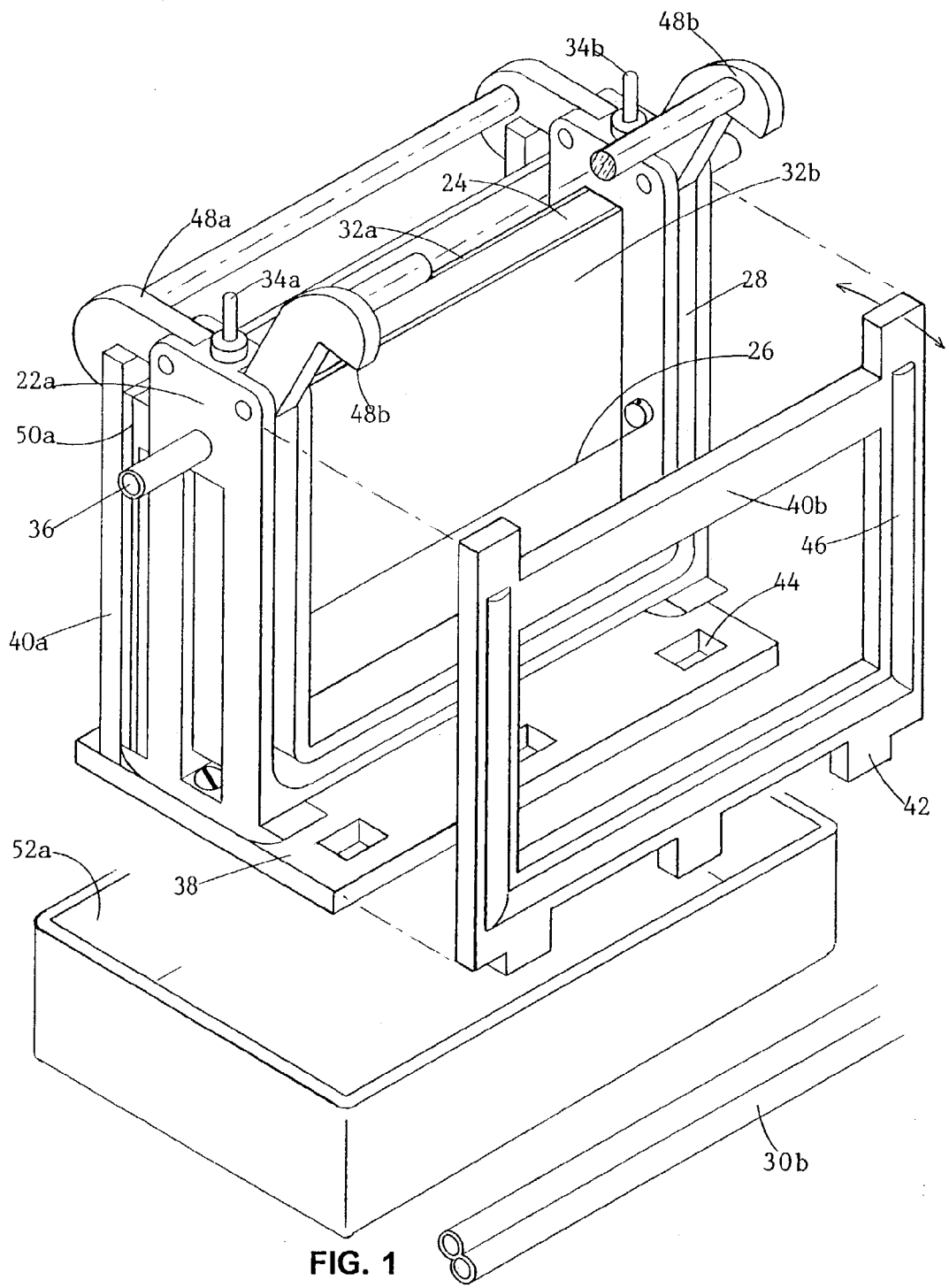
FIG. 1 is a perspective view of the improved VSGE cell 1.

FIG. 1 is a perspective view of the improved VSGE cell 1. Wherein UBC 22a has a flat cooling-chamber 24, which divides the UBC 22a into two compartments, each of them has an upper electrode 26 and a U-shaped side opening with a U-shaped groove 28 alongside it for a rubber sealing-gasket 30 to inlay in. Ceramic sheets 32a and 32b are the sidewalls, which are glued on the grids and the frame of the cooling-chamber 24. Banana plug 34a is for the upper electrode 26a, while 34b is for the lower electrode 62, which is hanged under the UBC 22a. One rubber sealing-gasket 30b has been pulled out off the U-shaped groove 28 in this drawing. In many embodiments of the present invention, the employed rubber sealing-gasket is formed by a rubber tubule that has an 8-shaped cross section as the 30b shown on the bottom of FIG. 1. This way formed rubber sealing-gasket has more elasticity and compressibility, so as to enable admit thickness different cassettes. The UBC 22a is affixed on the chassis 38, which has two lines of mortise 44s for the foot tenons 42s of the swing-frame 40 to insert in. Due to all the mortises 44s are loose mortises, so as to make the swing-frame 40a and 40b being swing-able, reversible and demountable. A predetermined gap is left therebetween of each swing-frame 40 and the U-shaped side opening it facing to. Swing-open a swing-frame 40 allows a cassette 50 to lower into the predetermined gap; swing-close the swing-frame can urge the cassette to abut to the UBC 22a tightly, hence the cassette/UBC complex is formed. Hasp 48b is a favorite holding means for holding the swing-frame 40 in the swing-closed state. As long as the formed complex (regardless one or two cassettes are assembled in) sets into a LBC 52a, thereupon the improved VSGE cell 1 is accomplished. Besieges, there is a U-shaped boss 46 sticking out from one face of each swing-frame 40, so as to makes the swing frame 40a and 40b being asymmetric from face to face. To reverse the swing-frame 40a and/or 40b inside face out can change the width of the gaps, so as to have some compatibility to those thickness different cassettes. Due to the cooling-chamber 24 divides the UBC 22a into two compartments, both the two upper electrodes 26 are positioned rather high in the UBC, and the employed LBC is shallow; therefore it allows unnecessary to block up the other side opening of the UBC when only a single gel runs in this kind dual gel cell. In FIG. 1, cassette 50a has been urged tightly abutting to the UBC 22a by the swing-frame 40a, while swing-frame 40b is shown in a demounted state.

Figure 2:
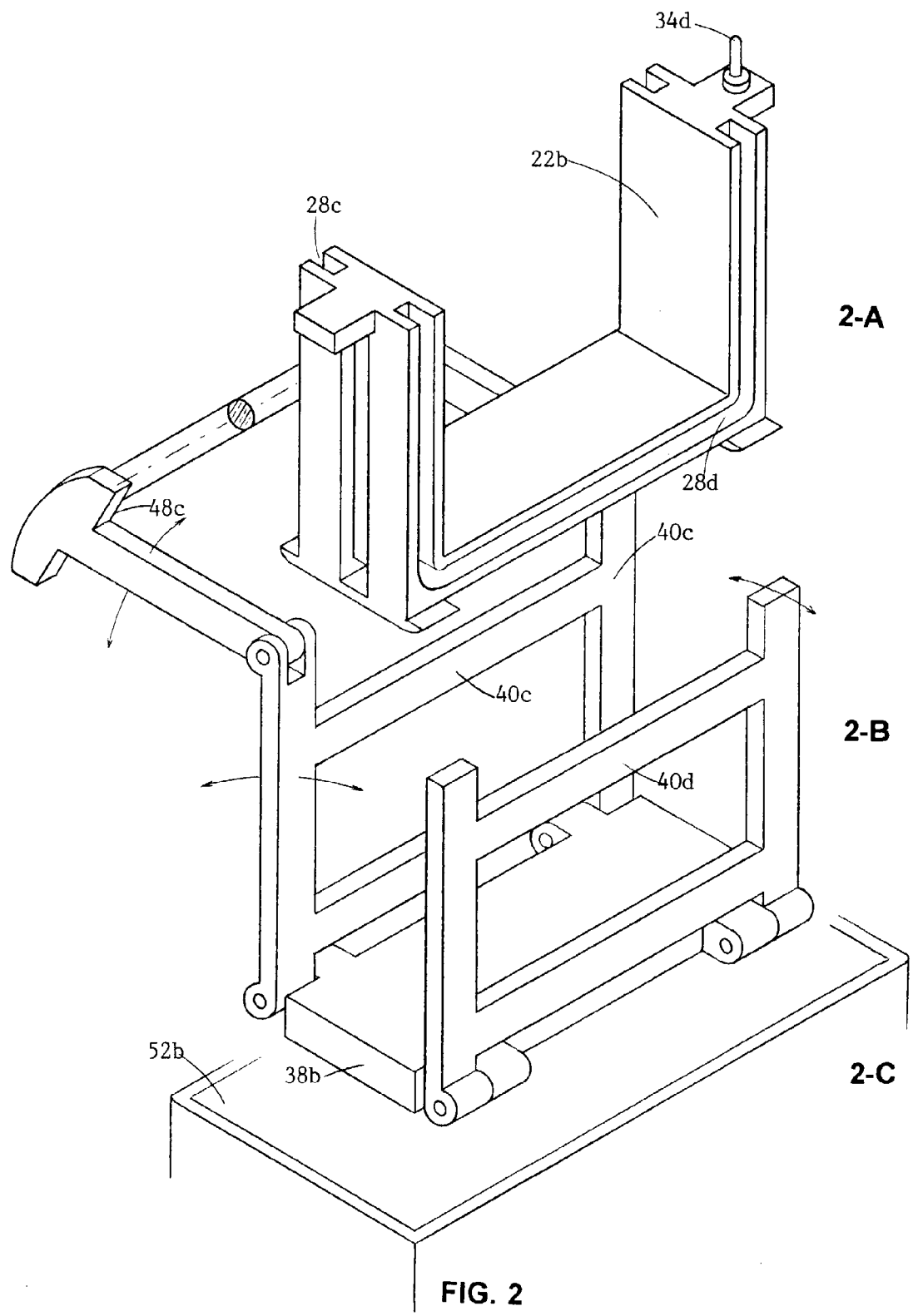
FIG. 2 is an exploded perspective view showing the structure of the improved VSGE cell 2.

FIG. 2 is an exploded perspective view illustrating the structure of the improved VSGE cell 2. Drawing 2-A shows the structure of UBC 22b, 34d is the banana plug for the lower electrode, 28c and 28d are two U-shaped groove for the rubber sealing-gaskets 30 to inlay in. Drawing 2-B shows the structure of the swing-frame-pair, which is formed by two swing-frames 40c and 40d, a chassis 38b and a hasp 48c. Wherein everything is articulated to each other, so that the whole swing-frame pair 2-B is invertable, and every part wherein is swing-able. After lowering the UBC 2A along with two cassettes into the swing-frame-pair 2-B, swing-close it, and holding it in the swing-closed state by the hasp 48c, thereupon a cassette/UBC complex is formed. As long as the formed complex seats into a LBC 52, and the heat adsorbing block 5-C (referring to FIG. 5) lowers into the UBC 2-A, thereupon the improved VSGE cell 2 is accomplished. The swing-frame-pair 2-B is invertable, that mines the span between the swing-frame 40c and 40d is adjustable, and this embodiment has some compatibility to those thickness different cassettes. That is because of the hubs are located biased, not located right on, the central line of the thickness of the swing-frame 40c and/or 40d. The swing-frame urging-mechanism disclosed in this and the above embodiments is novel, simple, flexible, easy to operate, and very compact. Therefore it allows using much smaller LBC, so as to reduce the pH buffer solution-using amount.

Figure 3:
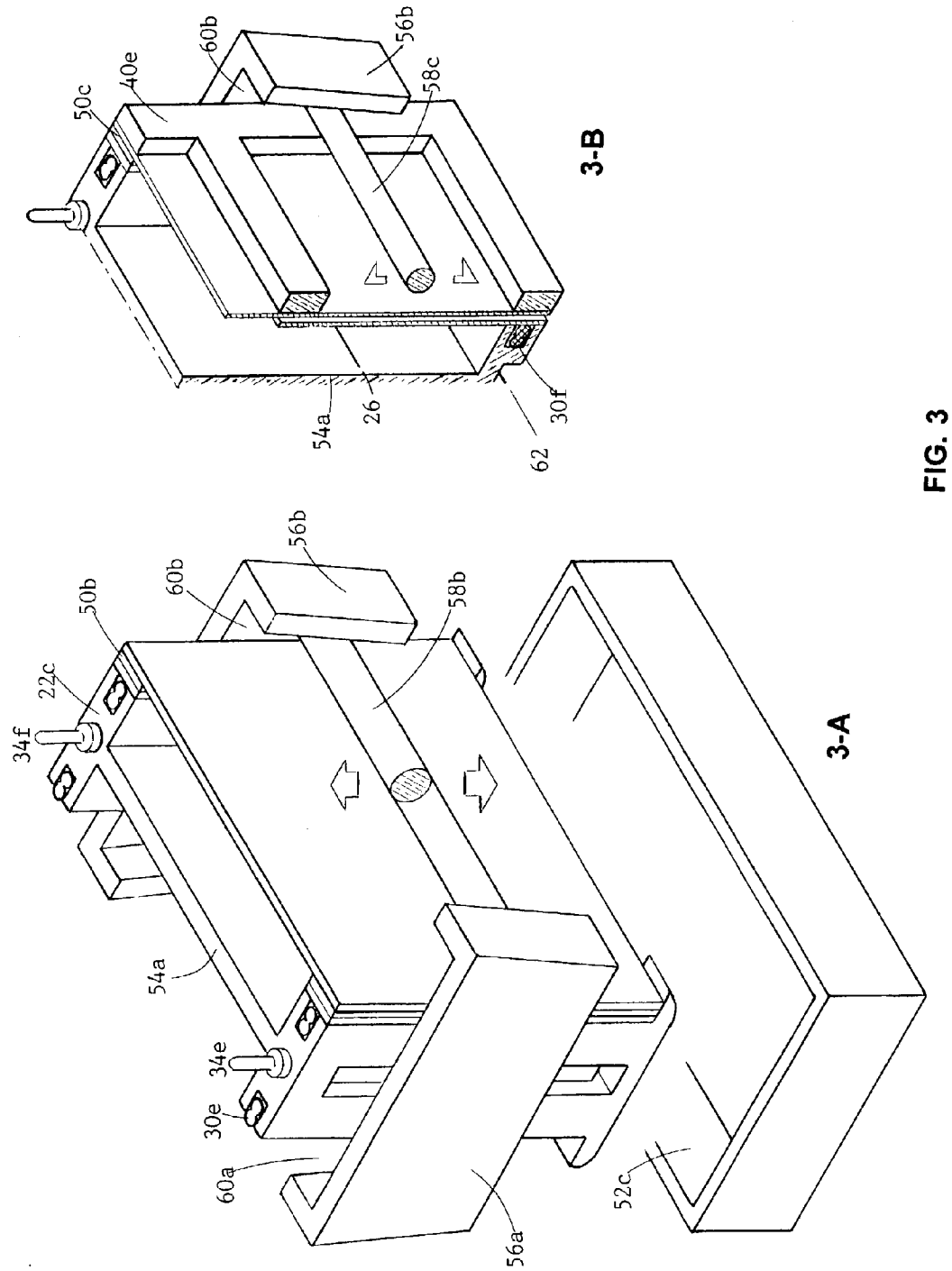
FIG. 3 is a set of perspective view illustrating the structure of the improved VSGE cell 3.

FIG. 3 is a set of perspective view illustrating the structure of the improved VSGE cell 3. In FIG. 3-A, UBC 22c has a septum-wall 54a, 30e and 30f are two rubber sealing-gaskets formed by the 8-sectioned rubber tubule as 30b, 50b is a cassette that has been urged tightly abutting to the UBC by the cylinder-beam 58b. The urging mechanism employed in this and the next embodiments is a trapezoidal-apron/cylinder-beam urging mechanism. Its principle is that by arranging a UBC along with two cassettes into a trapezoidal-apron, hence a V-shaped gap is formed therebetween when the apron is a right-angle trapezoidal-apron having one oblique sidewall; but two opposite V-shaped gaps are formed therebetween when the apron is a regular trapezoidal-apron having two oblique sidewalls. In the later case, affix the apron on the other two sides of the UBC. Thereafter, pushing a cylinder-beam into a V-shaped gap can urge the cassette(s) and the UBC to abut to each other tightly. Since the trapezoidal-apron is always affixed on some object, therefore it is better to split it into two trapezoidal half-aprons, as the 56a and 56b. So do can offer a great convenience to the operation, but without changing the function of the trapezoidal-apron. In FIG. 3-A, the two trapezoidal half-aprons 56a and 56b are formed by splitting a regular trapezoidal-apron into two pieces, and they are affixed aside the UBC 22c; the cylinder-beam 58b has been pushed into the V-shaped gap 60b, the cassette 50b has been urged to abut to the UBC 22c tightly. However, since usually a cassette itself is neither rigid nor strong enough, therefore it is better to interpose a rigidity frame 40e between the cassette 50 and the cylinder-beam 58 before it has been pushed into a V-gape, as shown in FIG. 3-B. Wherein 26 is the wire of the upper electrode, 62 is the wire of the lower electrode. Regardless two or one cassette is assembled in, the cassette/UBC complex is formed. As long as the formed complex sets into a LBC 52, thereupon the improved VSGE cell 3 is accomplished. To replace diameter different cylinder-beams can make the VSGE cell 3 being compatible with thickness different cassettes. By the same reason as mentioned above, it is unnecessary to block up the other side opening of the UBC, when there is only a single gel running in this dual gel cell 3.

Figure 4:
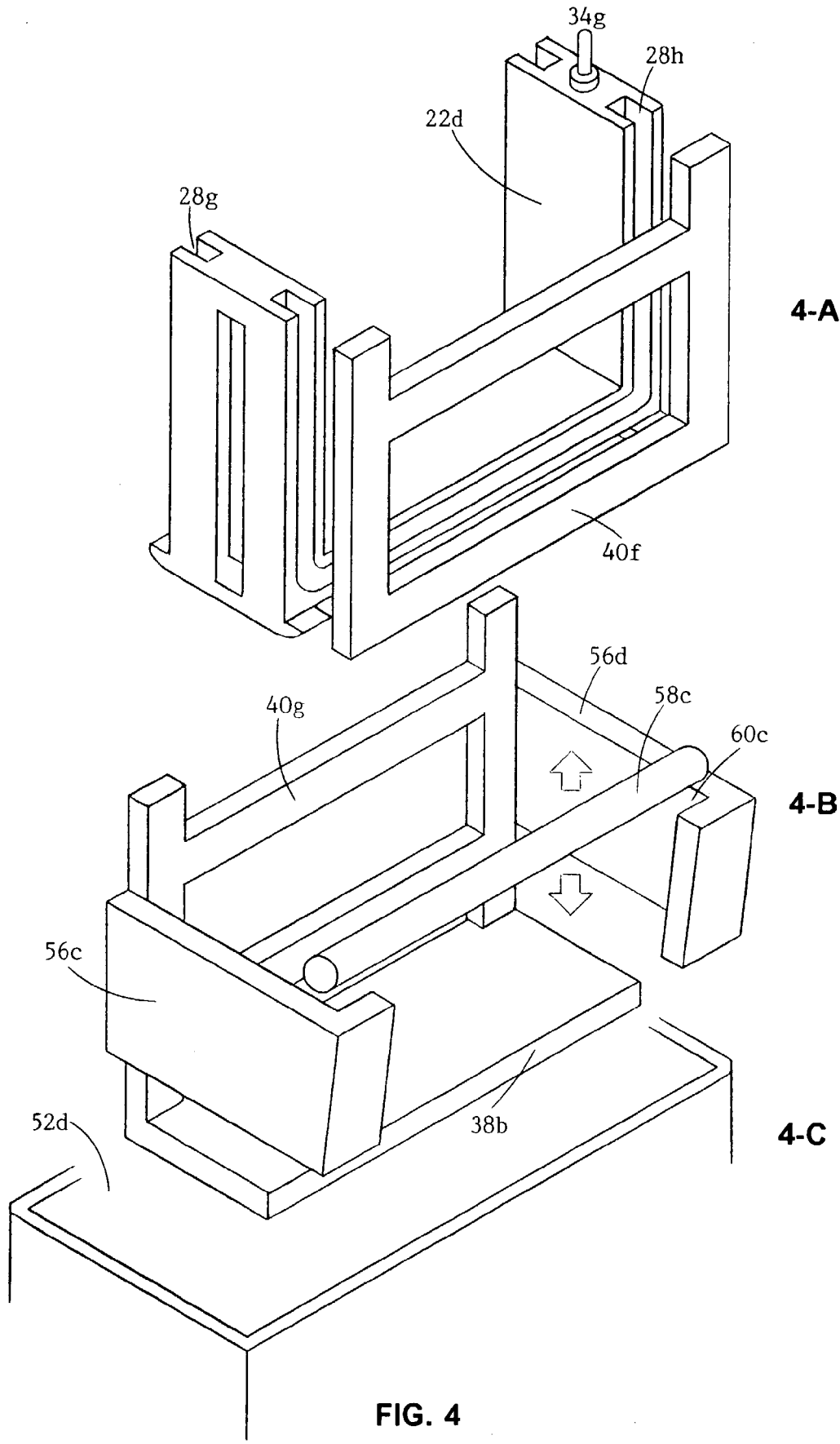
FIG. 4 is an exploded perspective view showing the structure of the improved VSGE cell 4.

FIG. 4 is a set of perspective view illustrating the structure of improved VSGE cell 4. Wherein 4-A shows the structure of the UBC 22d and the rigidity frame 40f. If overlooking the cylinder beam 58c, essentially 4-B is a right angle trapezoidal-apron, but has a wide vertical cut-off made on its oblique wall, so that two trapezoidal half-apron 56c and 56d are formed. The rigidity frame 40g forms the vertical sidewall of the apron 4-B, and 38b is the chassis. The method of using this embodiment is to hold the UBC 22d along with two cassettes plus the rigidity frame 40f in two hands of the operator, and lower them into the right-angle trapezoidal-apron 4-B, and then pushing the cylinder-beam 58d downward into the V-shaped gap 60c, thereupon a water-tightly abutted cassette/UBC complex is formed. After seating the formed complex into a LBC 52, and lowering the heat-adsorbing block 5-C (referring to FIG. 5) into the UBC 22d, thereupon the improved VSGE cell 4 is accomplished. This embodiment has the same advantage as that of the VSGE cell 3, but additionally has a heat-absorbing device.

Figure 5:
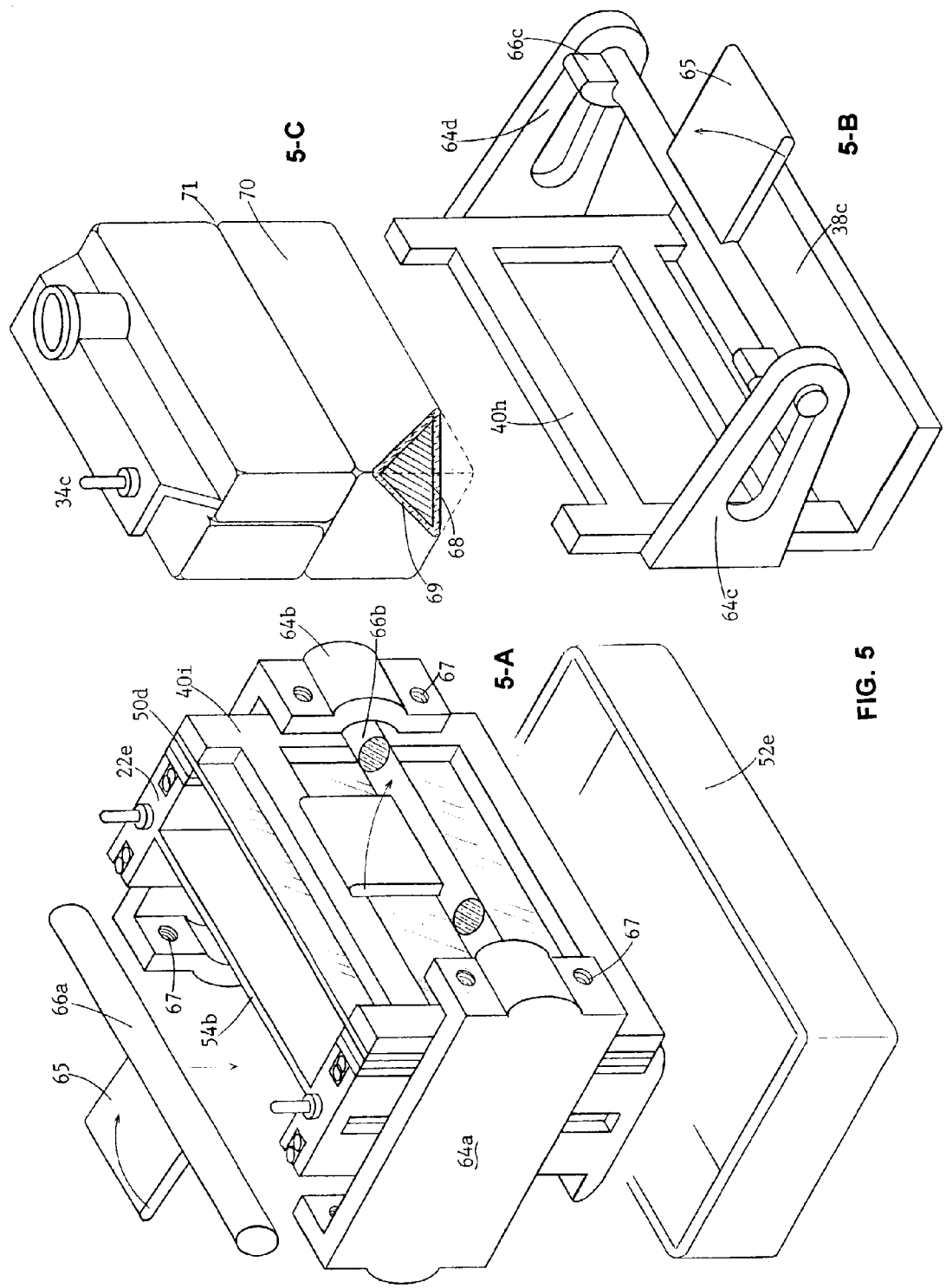
FIG. 5 is a set of perspective view illustrating the structure of the improved VSGE cell 5.

FIG. 5 is a set of perspective view illustrating the structures of the improved VSGE cell 5 and 5'. In FIG. 5-A, 22e is a UBC, 54b is its septum-wall, 64a and 64b are two side holding-arms, which are affixed aside the UBC for holding the cam-beams 66a and 66b aside the two U-shaped side openings respectively, but appropriate gaps are left therebetween. Cassette 50d and rigidity-frame 40i have been placed at their working positions, urged to tightly abut to the UBC 22e, so that the cassette/UBC complex is formed. As long as the formed complex seats into a LBC 52, thereupon the improved VSGE cell 5 is accomplished. As shown in this drawing, the cam-beams 66a and 66b both are demountable and replaceable, the 66a is in a demounting and turn-open state, but 66b is in its working position and is turned-close, each 65 is a lever for turning the cam-beam open or close. There are two ways to make this embodiment to compatible with thickness different cassettes. One way is to replace ellipticity different cam-beams; the other way is to use thumbscrews to urge the cassettes. Therefor eight screw holes 67s have been equipped on the four end-pieces of the two side holding-arms 67a and 67b in order to use the thumbscrews (not showing in this drawing). FIG. 5-B shows another embodiment of the cam-beam urging mechanism. Wherein, 38c is a chassis, 66c is a cam-beam (it is demountable and replaceable), which is held in its working position by two side holding-arms 64c and 64d, whereof the other ends are joined to a vertical rigidity frame 40h, so that the C-plus-I shaped structure 5-B is formed (by viewing from above) for accommodating the UBC and the cassettes. After lowering the UBC 22d (referring to FIG. 4-A) along with two cassettes plus the rigidity frame 40f into this C-plus-I shaped structure 5-B, and then turn-close the cam-beam 66c, thereupon another cassette/UBC complex is formed. As long as the formed complex sets into a LBC 52, and the heat-absorbing block 5-C lowers into the UBC 22d, thereupon the improved VSGE cell 5' is accomplished. FIG. 5-C shows the structure of the heat-adsorbing block 70, wherein 68 is a mass of gel ice (its alternative name is cellulose gum, its chemical composition is sodium methyl cellulose or some analogous) or a block of metal, 69 is an electric insulating crust, 71 is a groove for the upper electrode wire to inlay in, 34c is a banana plug. This heat-adsorbing block 70 should be kept in a freezer or any cooled enough place before using, and then be lowered into a UBC for absorbing the Joule-heat during electrophoresis. Additionally, block 70 can significantly reduce the using amount of the upper pH buffer solution, as well as allow the upper electrode 26 to mount thereon. Besides, heat-adsorbing block 70 also can be utilized in other kind electrophoresis cells, such as the so-called blotting cells, due to essential they are also gel electrophoresis cells, and wherein the gel slabs are vertically orientated.

FIG. 6 is a set of exploded perspective view illustrating the structures of the improved VSGC cassettes 6-A, 6-B and 6-C respectively. In cassette 6-A, 72a is a larger sidewall, 72b is a smaller sidewall, 74a and 74a' are a pair of flanged spacer strip; each of them has a flat spacer strip part with a flanged strip part aside it; the two flat spacer strip parts are clamped between the respective left and right margins of the two sidewalls 72a and 72a' so as to define a cavity between the four elements for the gel matrix to be cast in; while the two flanged strip parts rest on the respective left and right edges of the smaller sidewall 72b, so as to form a U-notched upper opening with even rim for the cassette (due to the flanged strip parts have the same thickness as the smaller sidewall), whereby enables the cassette 6-A to achieve a leak-free abutting to the UBC. Cassette 6-B is essentially same to the cassette 6-A, but herein the two flanged spacer strips 74b and 74b' are glued on the larger sidewall 72c, thus cassette 6-B is a two-element cassette; it still can have two glass and/or ceramics sidewalls. The spacer strips 74b and 74b' both can be formed by the extruded plastic strips, so as to reduce the cost. Polar plastic, such as PVC is a good material for making various spacer strips of the present invention, due to the gel matrix can adhere better to the polar plastic material. When a spacer strip is made of some kind flexible PVC, it can adhere on the sidewalls by itself, so as to offer great convenience for the cassette assembling, referring to the report (2); but hard PVC strips can be glued firmer on the sidewall. Sins the flanged spacer strips 74b and 74b' are glued on the larger sidewall 72c of cassette 6-B, therefore both of them also can be made of glass. The method is that first glues a narrower glass strip (as thick as the small sidewall 72d) onto a wider glass strip (its thickness defines the thickness if the gel casting cavity) to form a flanged spacer strip as the 74b, and then glues it on the larger sidewall 72c. Or quite the contrary, first glues a wider glass strip on the larger sidewall 72c, then glues a narrower glass strip atop the wider one to form the flanged spacer strip as the 74b. In cassette 6-C, the two flanged spacer strips 74c and 74c' are fused with the larger sidewall 72e. Since usually plastic spacer strips cannot to fuse with a glass sidewall, therefore when we say some spacer strips are fused with a sidewall in this document, it means that both of them are integrated formed either by molded injecting plastic, or by die pressing glass (as making a glass ashtray). In addition, when we say some spacer strips are affixed on a sidewall, it means that the spacer strips can either be glued on the sidewall, or are fused with the sidewall. Cassette 6-C is also a two-element cassette, wherein the flanged spacer strip 74c and 74c' are integrated formed with the larger sidewall 72e. Since it must be molding formed, therefore it allows some small modification to be made on the mold without increasing the cost. Actually, the four 45 degree transition angles are made at the upper and lower end positions of the two flanged spacer strips 74c and 74c', as showing in FIG. 6-C. And correspondingly, the four corners of the smaller sidewall 72f have been ground off The advantage of doing such a small modification is due to it can restrain the smaller sidewall 72f from sliding to any direction. Regardless the larger sidewall is plastic or glass, the smaller sidewalls in cassette 6-A, 6-B or 6-C still can be ceramic or glass, since they are the inner sidewalls, facing to the UBC, unnecessary to be transparent.

FIG. 7 is a set of fragmentary perspective view illustrating the structures of the improved VSGC cassettes 7-A and 7-B. In cassette 7-A, the U-shape flanged spacer 76 is formed by linking the two flanged spacer strips 74a and 74a' (as in cassette 6-A or 6-B) to each other by a flanged spacer strip beam adjoined therebetween at their two lower ends. Therefore a U-shaped flanged spacer is formed, which has two upward sidearm and a bottom horizontal beam. The flat spacer part of the horizontal beam portion has degenerated into one shark tooth 78 for clipping between the lower margins of the two sidewalls 72g and 72h, so as to increase the compression strength of the bottom margin area (the mastoid 84 of cassettes 7-B and the mastoids in the two-element cassettes, as in cassette 9, cassette 11, cassettes 6-B and 6-C, all have the same function as the shark tooth 78); while the flanged part of the horizontal beam portion has narrowed down approximately 1 to 2 mm from its top edge, but except the very left and very right two tab areas, which rest on the respective very left and very right ends of the bottom edge of the smaller side wall 72h. As a result, the lower opening 80 has been diverted from usually downward direction into the abutting face direction of the cassette 7-A or cassette 7-B. This U-shaped flanged spacer 76 is glued on the larger sidewall 72g in cassette 7-A, but the U-shaped flanged spacer 76' is fused with the larger sidewall 72g' in cassette 7-B. Thereafter, the only two remaining assembling seams 82, 82' and the lower opening 80 are all located on the abutting face of cassette 7-A or cassette 7-B. This characteristic of cassette 7-A and 7-B is valuable, but only if it is aware. The value is the assembling seams 82, 82' and the lower opening 80 of cassette 7-A and 7-B can be sealed up simultaneously by resting a U-shaped rubber sealing gasket on them for gel casting.

FIG. 8 is a set of front view showing the position relationship of the U-shaped rubber sealing-gasket versus the cassette 7-A or 7-B during gel casting or electrophoresis running respectively. Wherein 8-A shows that the U-shaped rubber sealing-gasket 30 ought to rest on the two vertical assembling seams 82 and 82' as well as on the lower opening 80 of the cassette 7-A or 7-B during performing the gel casting. However, when the U-shaped rubber-sealing gasket 30 is a part of a VSGE cell, it means that the cassettes 7-A and 7-B can undergo the gel casting within the VSGE cell, and subsequently to carry out the electrophoresis just by shifting the cassette downward for a little distance, as shown in FIG. 8-B. It is worth to point out that although there are two vertical assembling seams 82 and 82' on the abutting faces of cassette 7-A or 7-B, but no upper pH buffer solution can leak out by either along or across them during electrophoresis running. That is because of the assembling seam 82 and 82' are also filled with gel matrix, after the gel matrix to be cast into the cassette by using our gel casting method; besides, the rubber sealing-gasket 30 always rests on the assembling seam 82 and 82' during electrophoresis running. This situation is also true to all the cassettes 6-A, 6-B, and 6-C as well as to the cassette 10 and cassette 11.

Figure 9:
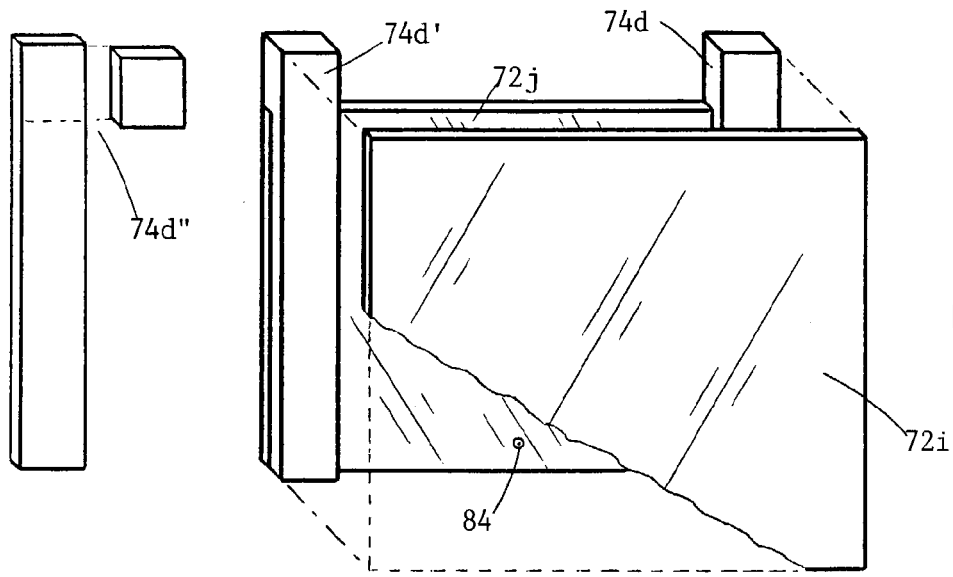
FIG. 9 is an exploded fragmentary perspective view showing the structure of the improved VSGC cassettes 9.

FIG. 9 is an exploded perspective view of the improved VSGC cassette 9. Wherein 72i is a longer sidewall, 72j is a shorter sidewall, 74d and 74d' are two flanged spacer strips; each of them has a flat spacer strip part with a flanged tab part atop it, Thereof the two flat spacer strip parts are clipped between the respective left and right margins of the two sidewalls 72i and 72j, while the two atop flanged tab parts rest atop the respective left and right ends of the top edge of the shorter sidewall 72j. The flanged spacer strips 74d and 74d' are glued on, or fused with, the shorter sidewall 72j, but leaving the longer sidewall 72i demountable. Cassette 9 still can have two glass and/or ceramic sidewalls if the spacer strips are glued on the shorter wall. Each of the flanged spacer strips 74d and 74d' can be an integrated one piece as showing in the drawing, but also can be formed by a flat spacer strip of plastic or glass with a square tab of plastic or glass to be glued on it, as the 74d''.

Figure 10:
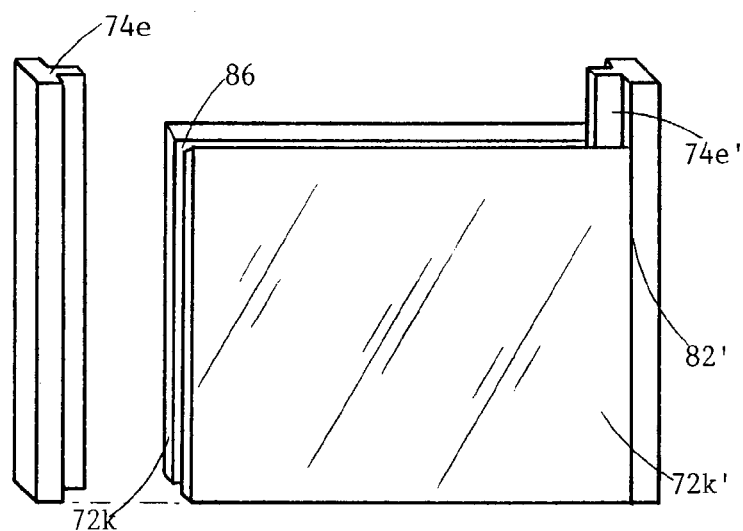
FIG. 10 is an exploded perspective view of the improved VSGC cassette 10.

FIG. 10 is an exploded perspective view of the improved VSGC cassette 10. Wherein 72k and 72k' are two identical sidewalls, 74e and 74e' are a pair of flanged spacer strips; each of them has a T-shaped cross section. Whereof the two flat spacer strip parts are clamped between the respective left and right margins of the two identical sidewalls 72k and 72k', while the two T-head parts rest on the respective left and right side edges of the two identical side walls, then a U-notched upper opening is formed simply due to the spacer strips are longer than the sidewalls. Herein the formed U-notched upper opening exposes to the two opposite face directions of cassette 10. The two spacer strips 74e and 74e' are allowed to affix on any one of the two sidewalls. Besides, both of the upper inner angles of the glass sidewalls 72k and 72k' are ground off, so as to form a V-shaped beak 86 within the U-notched upper opening of this kind cassette.

Figure 11:
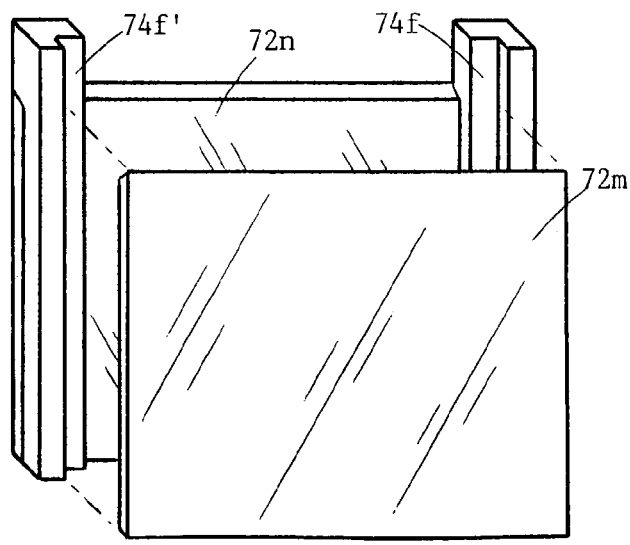
FIG. 11 is an exploded perspective view of the improved VSGC cassette 11.

FIG. 11 is an exploded perspective view of the improved VSGC cassette 11. Wherein 72m is a narrower sidewall, 72n is a wider sidewall, 74f and 74f' are a pair of flanged spacer strip; each of them has a flat spacer strip part with a flanged tab part atop it on one face, while with a flanged strip part aside it on the other face. Whereof the two flat spacer strip parts are clamped between the respective left and right margins of the two side walls 72m and 72n, the two atop flanged tab parts rest on the respective left and right ends of the top edge of the wider sidewall 72n, while the two aside flanged strip parts rest on the respective left and right edges of the narrower sidewall 72m. The two spacer strips 74f and 74f' are affixed on the wider sidewall 72n, but leaves the narrower sidewall 72m being demountable. This cassette also can have the V-shaped beak 86 as the cassette 10, and still can have two glass and/or ceramic sidewalls when the two spacer strips are glued on the wider sidewall. Cassette 10 and 11 are ideal for the $2^{nd}$-D electrophoresis running of the 2-D gel electrophoreses method. Because, each of these cassettes has two abutting faces, whereby can form an infinite cassette/UBC complex by alternately abutting with appropriate UBC modules. In addition, the V-shaped beak 86 provided an advantage that allows using a much thicker gel cylinder to run the $1^{st}$-D isoelectric focusing of the 2-D gel electrophoreses, so as to significantly enhance the sensitivity of the 2-D gel electrophoresis analysis method.

Figure 12:
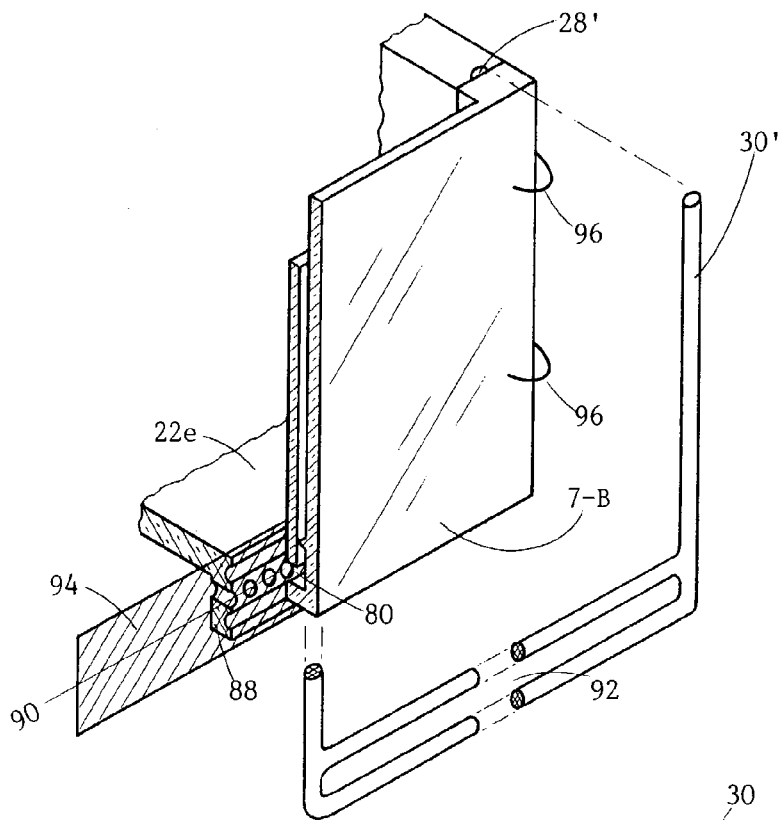
FIG. 12 is an exploded fragmentary perspective view showing a way to modify an ordinary UBC as well as an ordinary U-shaped rubber sealing-gasket, so as to enable the cassette 7-A or 7-B to undergo the gel casting in situ exactly at their electrophoresis running position.

FIG. 12 is an exploded fragmentary perspective view diagramming a way to modify a regular UBC as well as a regular rubber sealing-gasket in order to make the cassettes 7-A or 7-B can undergo the gel casting in situ exactly at their electrophoresis running position. Wherein the modification includes that; on one hand, makes each U-shaped side opening of an ordinary UBC to have a downward, coplanar and penetrable lip 88, by such as punching a row of small hole 90 thereon; on the other hand, splits the horizontal beam part of a regular U-shaped rubber sealing gasket into two strands, so as to form a horizontal loop 92 at the bottom of the modified U-shaped rubber sealing gasket 30'. After inlaying the modified rubber sealing gasket 30' into the modified U-shaped groove 28', the lower horizontal loop 92 just loops around the row of small hole 90. However, for showing all things clearly in a single drawing, the modified rubber sealing gasket 30' has been pulled out off the modified U-shaped groove 28', as shown in FIG. 12. The way to use this embodiment is that firstly to adhere a strip of water dipped semipermeable membrane 94 aside the horizontal loop 92, and then to force the cassette 7-A or 7-B to rest on the modified UBC 22e by aiming the lower opening 80 of the cassette at the row of small hole 90. As a result, the semipermeable membrane 94 is tightly clamped therebetween, functionally to seal up the lower opening 80 of the cassette 7-B or 7-A. This embodiment enables the cassettes 7A or 7-B to undergo the gel casting in situ exactly at theirs electrophoresis running position, and subsequently to carry out the electrophoresis without need to move or remove anything. Although 30 years ago in U.S. Pat. No. 3,419,580, a semipermeable membrane had been employed to seal up the lower opening of the gel-casting cavity of the VSGE cell. However, there was no independent gel-casting cassette in that VSGE cell, and wherein the semipermeable membrane was a build-in part of the VSGE cell, so it was not easy to be replaced from time to time.

Figure 13:
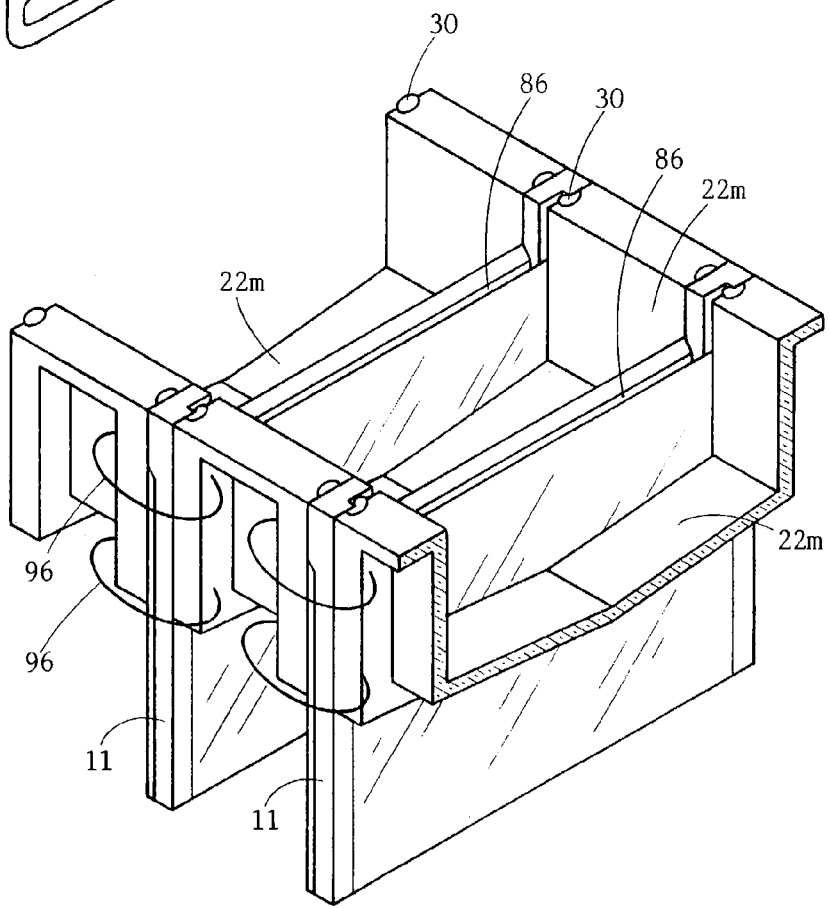
FIG. 13 is a perspective view of a segment of the multiple cassette/UBC complex 13.

FIG. 13 is a perspective view of a segment of the infinite cassette/UBC complex 13. Wherein each 11 is a cassette 11 or a cassette 10, each 22m is a UBC module, each 86 is a V-shaped beak of the cassette, and each 96 symbolizes a clamping means. This drawing shows that by abutting the cassette 10 or 11 alternately with the UBCm modular can form an infinite cassette/UBC complex. This complex 13 can be extended as long as required, and stooped at any length by clamping two plastic plats at the two ends respectively. This embodiment can guarantee a numerous vertical slab gels to carry out the electrophoresis parallel in it under an identical condition. Therefore it is ideal for multiple the 2nd-D electrophoresis running of the 2-D gel electrophoreses simultaneously.

FIG. 14 is a set of front view showing a method for snugly encasing the VSGC cassettes into a plastic membrane pouch for gel casting. The method is that firstly to place one or several pieces of face-to-face arranged cassettes 50 into a roomy plastic membrane pouch 100a, which has a lower softening point; then using some means to hold the open mouth area of the pouch, so as to prevent the mouth area from over shrinking; and then using a hot air blower to blow the plastic pouch 100a causing it shrinking. Thereafter the pouch 100a snugly wraps around the cassettes 50. After removing the holding means, the cassettes 50 are ready to be sandwiched between two splints for gel casting. This method is good for encasing any sized VSGC cassettes for gel casting. FIG. 14-A shows that a wide camp 96w is employed to hold the open mouth. FIG. 14-B shows that by partially fusing the open mouth area, such as the 98 labeled area, and then to cut it off after shrinking.

FIG. 15 is a set of front view showing a method for snugly encasing the VSGC cassettes into an elastic membrane pouch for gel casting. Wherein 50 is one or several pieces of face-to-face arranged cassettes, but are placed upside-down; 100b is an elastic membrane pouch that has a tail tubule 110a at the bottom, and its cuff area has been curled up, so that a thicken beaded cuff 102 is formed; 104 and 104' are two fingers, or any kind of stretching means, for propping up the elastic pouch 100b until it is expanded wide enough. Then wraps the expanded elastic pouch 100b around the cassettes 50, as showing in FIG. 15-A. After removing the stretching means, releasing the beaded cuff 102 as showing in FIG. 15-B, and turning the cassettes right side up, thereupon the cassettes 50 are ready for the next step of gel casting. For the gradient gel casting, the gel forming solution should be injected into the pouch 100b via its tail tubule 110a (referring to FIG. 18). For regular uniform gel casting, the elastic membrane pouch needs not to have the tail tubule 110a.

Figure 16:
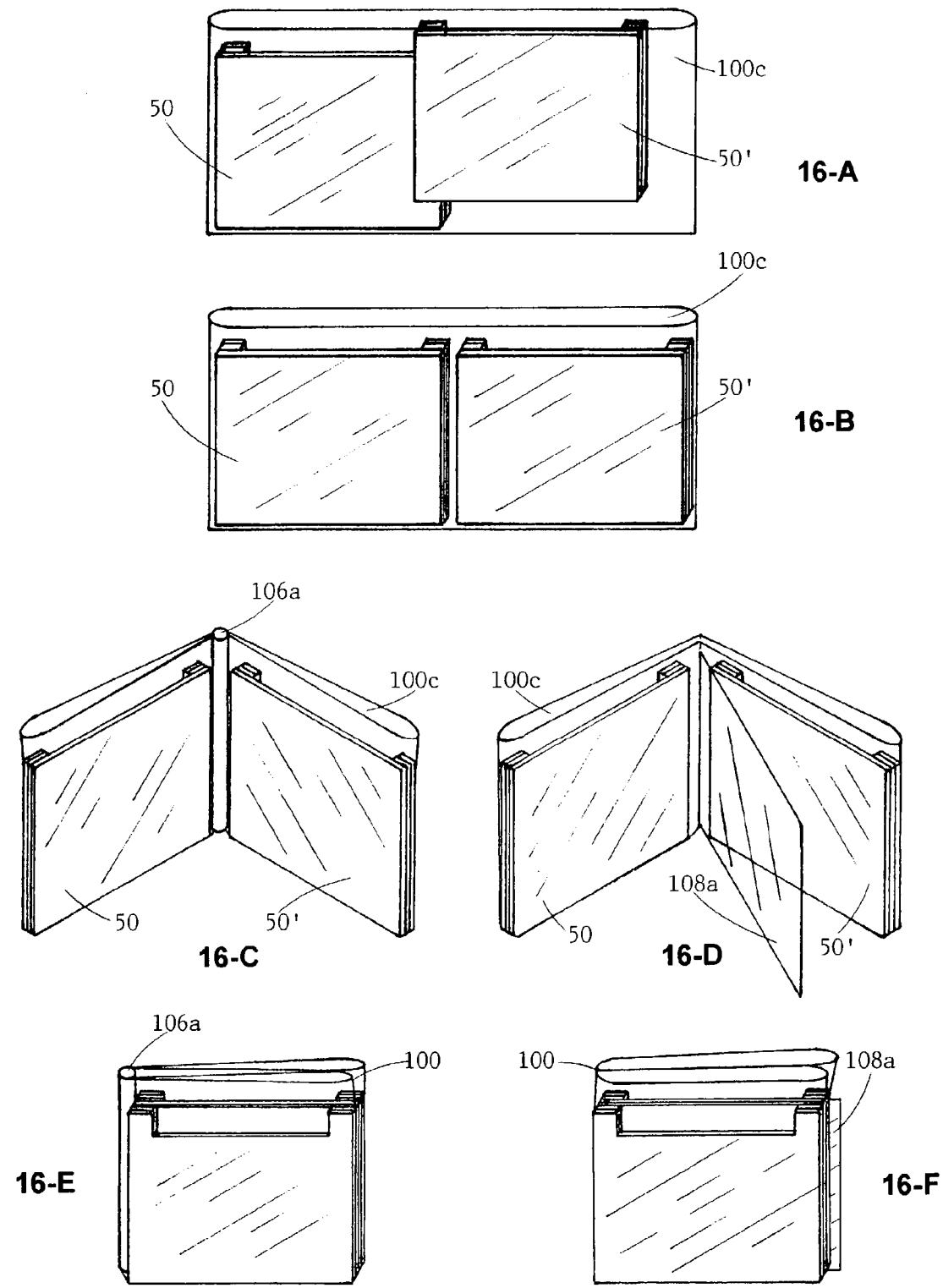
FIG. 16 is a set of perspective view showing a method for snugly encasing two VSGC cassettes into an ordinary plastic membrane pouch for gel casting.

FIG. 16 is a set of perspective view showing a method for snugly encasing two VSGC cassettes into an ordinary plastic membrane pouch for gel casting. In FIG. 16-A, two cassette 50 and 50' have been placed into a size appropriate ordinary plastic membrane pouch 100c. FIG. 16-B shows that the cassette 50 and 50' have been arranged to be side-by-side. FIG. 16-C and 16-D shows that a propping means, such as a plastic stick 106a or a plastic card 108a, has already rested on the central line of the pouch 100c. While FIG. 16-E and 16-F show that by using the propping means as an inflection point to fold up the plastic pouch 100c until the cassette 50 and 50' from side-by-side became face-to-face. Thereafter, the cassette 50 and 50' are snugly incased in the pouch 100c, and ready for the next step of gel casting. FIG. 16 disclosed a very convenient method to snugly encase two cassettes at once for gel casting. General specking, placing n piece cassettes (n>1) side-by-side into an appropriate membrane pouch, then using n−1 pieces propping means from outside to rest on the pouch at the positions between each two neighboring cassettes, then by using the propping means as the inflection points to zigzag fold up the membrane pouch until all the cassettes from side-by-side became face-to-face, thereupon those cassettes are ready for the next step of gel casting.

Figure 17:
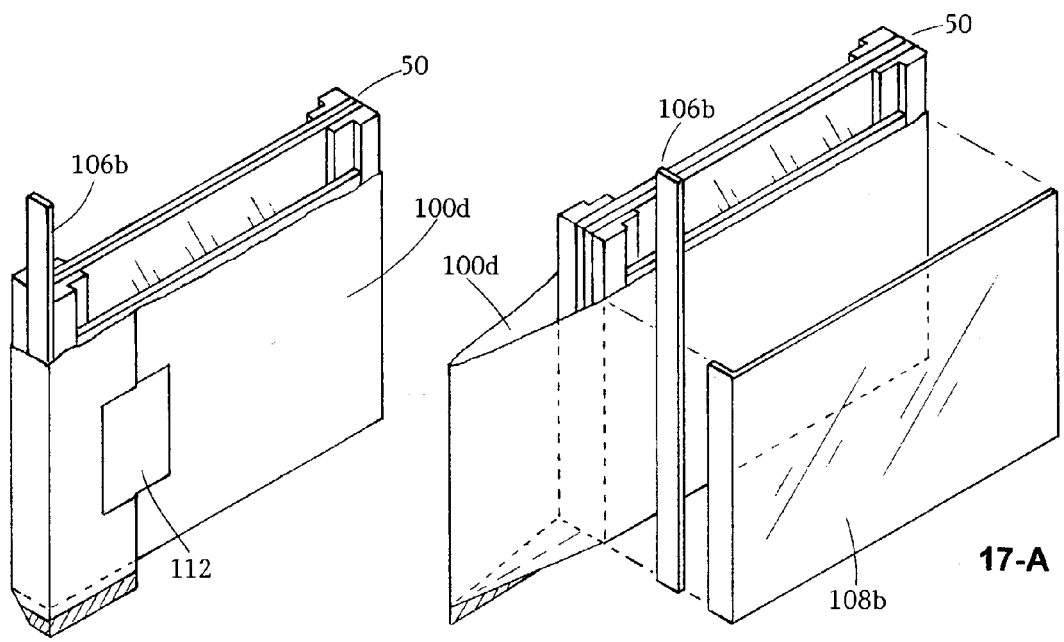
FIG. 17 is a set of perspective view showing a method for snugly encasing the VSGC cassettes into an ordinary plastic membrane pouch for gel casting.

FIG. 17 is a set of perspective view showing a method for snugly encasing the VSGC cassettes into an ordinary plastic membrane pouch for gel casting. Wherein 17-A shows that one or several pieces of face to face arranged cassettes 50 have been placed into a roomy plastic membrane pouch 100d, and have been moved to one side of the pouch. A propping means, such as the plastic stick 106b, or the bent edge of the plastic card 108b, is employed to rest on the pouch 100d at the position as close as to the cassettes. Then the method is using the propping means as a point of inflection to fold the remainder of the pouch 100d towards the cassette side, and to hold it in such a folding state by such as a piece of adhesive tape 112, as shown in FIG. 17-B. Thereafter the cassettes 50 are snugly incased in the pouch 100d, and ready for the next step of gel casting. This method is very convenient and flexible. Besides, it also can be used to cast the gradient gels, provided the employed plastic membrane pouch has a tail tubule at the bottom (referring to FIG. 18).

Figure 18:
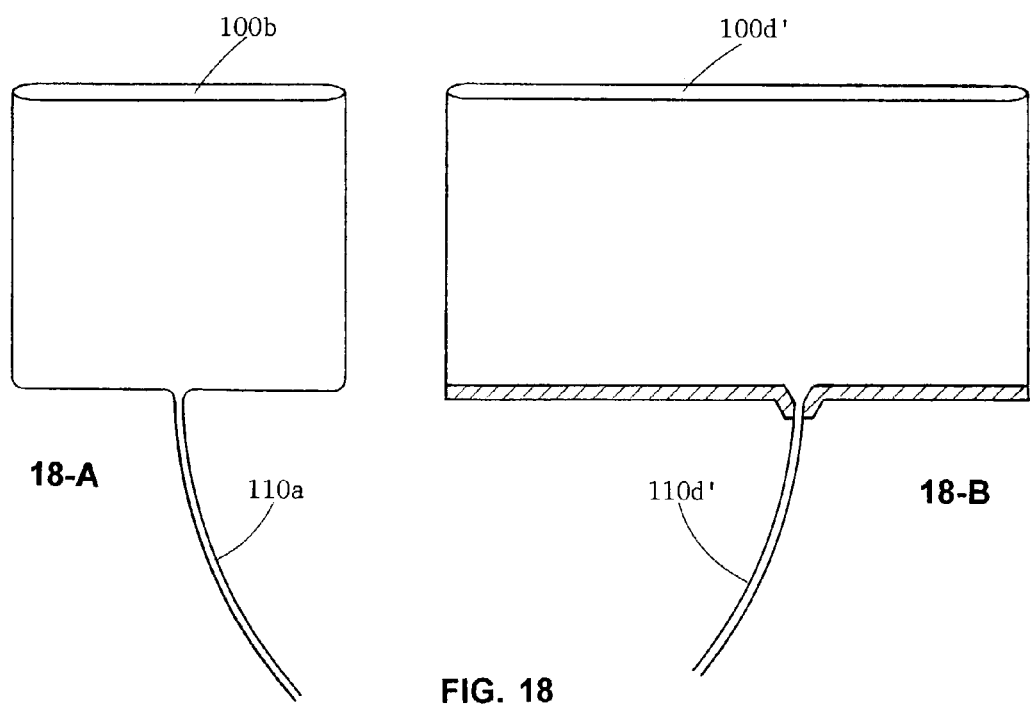
FIG. 18 is a set of front view showing the structure of the membrane pouch 18-A and 18-B.

FIG. 18 is a set of front view showing the structure of the membrane pouches, each of them has a tail tubule. FIG. 18-A shows the structure of the elastic membrane pouch 100b, 110a is its tail tubule. FIG. 18-B shows the structure of the inelastic membrane pouch 100d', 110d' is its tail tubule.

Figure 19:
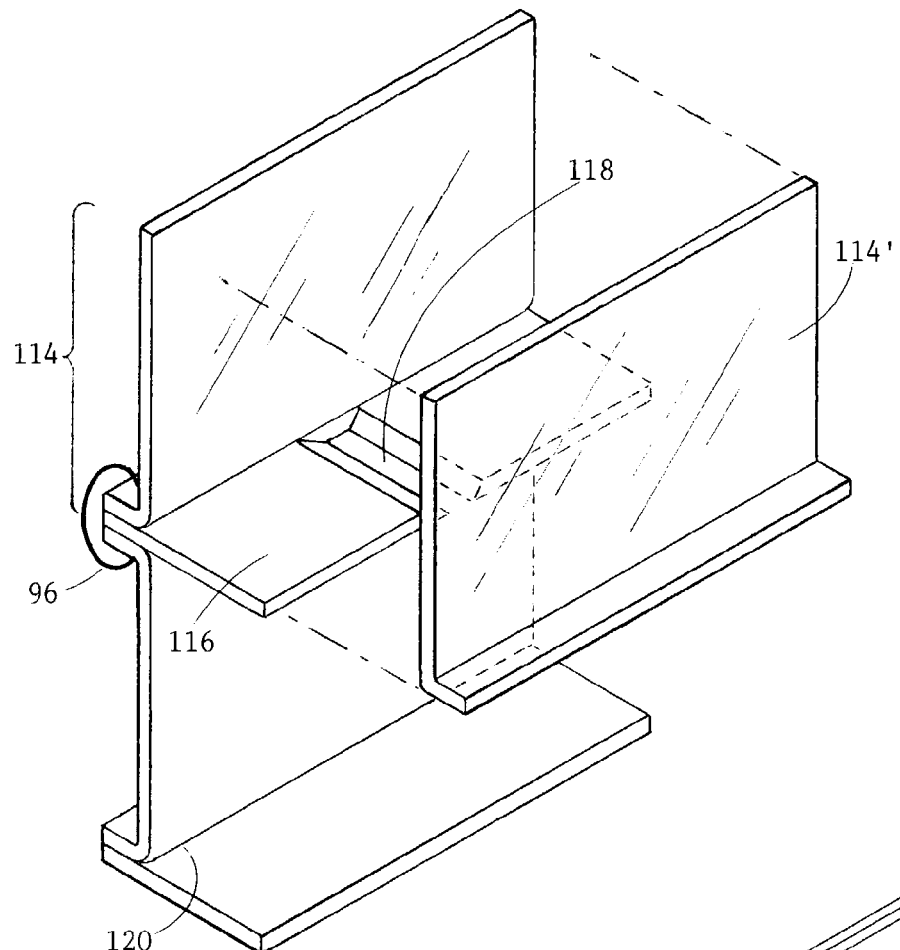
FIG. 19 is a perspective view of the splint pair 19 employed for gel casting.

FIG. 19 is a perspective view of the splint pair 19 employed for gel casting. Wherein 114' is a movable splint, 114 is a immovable splint that has a base plate 116 attached under it, 118 is a V-shaped cut off formed on the base pleat 116 for the tail tubule 110 to pass through, 120 is a bottom stand for raising up the splint pair 114 and 114' atop it, so as to perform the gradient gel casting; and each 96 symbolizes a clamping means.

Figure 20:
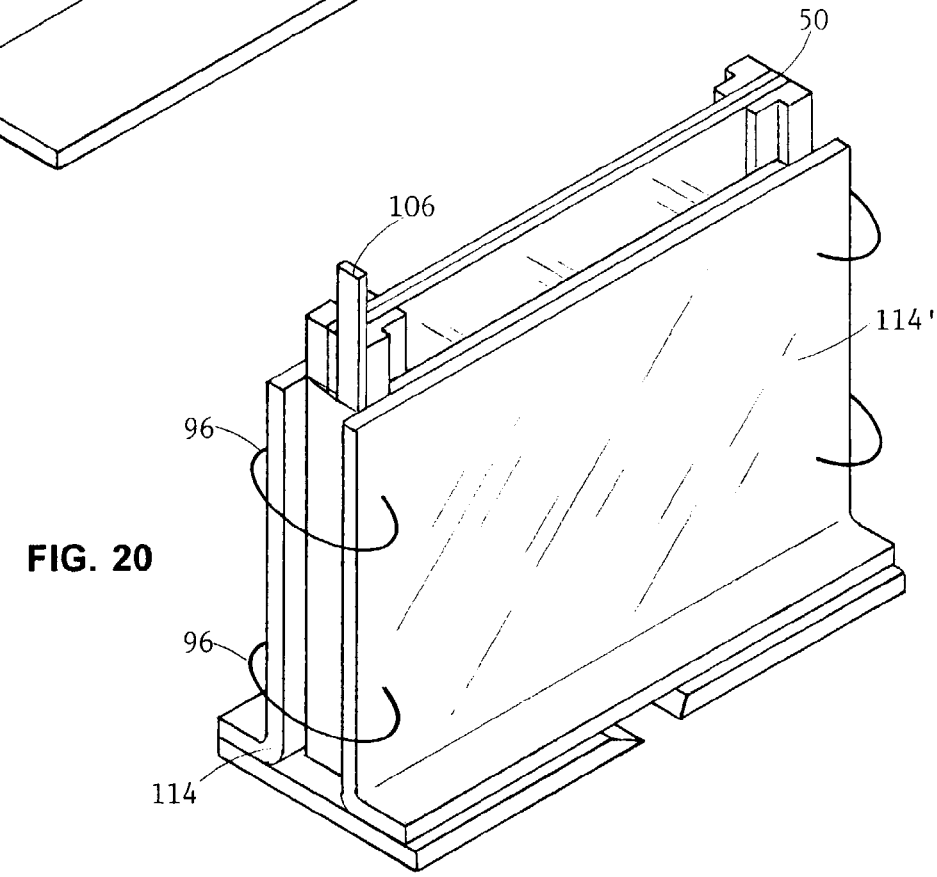
FIG. 20 is a perspective view illustrating the method of sandwich those pouch snugly encased cassettes between the splint pair 19 for gel casting.

FIG. 20 is a perspective view showing the way to sandwich the VSGC cassettes between the splint pair 19 for gel casting. Wherein 50 are the cassettes that have been snugly incased in a membrane pouch; 114 and 114' is a splint pair, each 96 symbolizes a clamping means. For performing regular uniform gel casting, the gel forming solution can be poured into the cassettes from their upper openings. For performing the gradient gel casting, the splint pair 114 and 114' should be raised atop the bottom stand 120, as showing in FIG. 19, the employed pouch should have a tail tubule 110 at the bottom (referring to FIG. 18), and the gel forming solution should be injected into the pouch via its tail tubule 110.

After review the specification and the drawings, it is obvious that almost all aspects, but the structural style, about the VSGE cells and related methods have been improved in the present innovations. So the present innovated VSGE cells are still belong to the most popular styled VSGE cells, as mentioned in the background paragraph. Since the most popular styled VSGE cells are very familiar to every manufacturer as well as to every laboratory technician, so that there is no necessary to point out which face of the cassette is the abutting face that should to be used to abut to the UBC, where of a UBC the cassette should to be abutted at, etc. In addition, when we say two cassettes abut to a UBC, it means that the cassettes are forced to rest on the two U-shaped rubber sealing-gaskets of the UBC respectively, or means that the two cassettes are forced to sandwich a UBC between them.

What is claimed is:

1. A vertical slab gel electrophoresis instrument for carrying out electrophoretic separation vertically within substantially upright arranged slab-shaped gel media comprising:
   (i) an upper buffer chamber for housing a volume of upper pH buffer solution and an upper electrode in it, having base plate, sidewalls and at least one U-shaped side-opening that is rimmed alone with a U-shaped rubber sealing gasket so as to enable a vertical slab gel cassette to join thereat water tightly;
   (ii) said vertical slab gel cassette is for said gel to be cast in it and said electrophoretic separation taking place therein, having two spacer spaced sidewalls, closed left and right edges, a lower opening and a U-notched upper opening;
   (iii) an urging mechanism for forcing said cassette to join said upper buffer chamber at its U-shaped side-opening, so as to form a cassette/upper buffer chamber complex with the U-notched upper opening of said cassette exposing to the inside of said complex;
   (iv) a lower buffer chamber having base plate and sidewalls for housing a volume of lower pH buffer solution, a lower electrode and at least one lower opening of said cassette in it;
   (v) a heat absorbing device for absorbing Joule-heat during an electrophoresis run; and
   (vi) means for preventing the gel from leaking when said gel is cast into said cassette;
   wherein the improved urging mechanism comprising:
   (a) at least a swing-frame and a hooking means;
   (b) a portion of said swing-frame is arranged to face to a U-shaped side opening of said upper buffer chamber, but an appropriate interval is left there between the portion of said swing-frame and the U-shaped side opening of said upper buffer chamber;
   (c) said swing-frame is swingably coupled on a chassis, which is located under said upper buffer chamber;
   (d) when said swing-frame is in a swing-opened state, it allows said vertical slab gel cassette to be inserted into said interval; and
   (e) when said swing-frame is in a swing-closed state and is held in such a swing-closed state by said hooking means, said swing-frame is forcing said cassette to join said upper buffer chamber.

2. The electrophoresis instrument of claim 1, wherein the improved heat absorbing device comprising:
   (a) a mass of material selected from the group consisting of metal and gel ice;
   (b) said mass of material is sealed in a dielectric shell, and is stored in a lower temperature environment before and after using it; and
   (c) said heat absorbing device is lowered into said upper buffer chamber for absorbing the Joule-heat during said electrophoresis run.

3. The electrophoresis instrument of claim 1, wherein the improved U-shaped rubber sealing gasket is formed by an elastic rubber tubule that has an 8-shaped cross section.

4. A method of using the electrophoresis instrument of claim 1 comprising:
   (a) tightly enclosing at least one of said vertical slab gel cassettes into a membrane pouch, but leaving the upper mouth of said pouch open; and
   (b) sandwiching the enclosed cassette between a pair of splints, thereupon said cassette is ready to undergo said gel casting without leaking.

5. The method of claim 4, wherein said method further comprises the steps of
   (a) placing at least one of said vertical slab gel cassette into a roomy plastic membrane;
   (b) using a holding means to hold-up the upper open mouth of said membrane pouch at a position above said cassette;
   (c) exposing the pouch enclosed cassette to an appropriate higher temperature, so as to cause said membrane pouch shrinking and hereby to tightly enclose said cassette in it; and
   (d) removing said holding means after said cassette cools down.

6. The method of claim 4, wherein said method further comprises the steps of:
   (a) placing at least one of said vertical slab gel cassette into a roomy plastic membrane pouch, then moving said cassette toward one side of said pouch; and
   (b) using a propping means from outside to rest upon said membrane pouch at the position close to said cassette, then folding a portion of said membrane pouch towards the cassette side and holding it in such a folding state, thereupon said cassette is ready for the next stage of gel casting.

7. The method of claim 4, wherein said method further comprises the steps of:
   (a) using a stretching means to stretch-up an elastic membrane pouch until it is expanded larger;
   (b) placing at least one of said vertical slab gel cassette into the expanded elastic membrane pouch; and
   (c) removing said stretching means, allowing said elastic membrane pouch to shrink back and tightly enclose said cassette within it, said cassette is thereby ready for the next stage of gel casting.

8. A vertical slab gel electrophoresis instrument for carrying out electrophoretic separation vertically within substantially upright arranged slab-shaped gel media comprising:
   (i) an upper buffer chamber for housing a volume of upper pH buffer solution and an upper electrode in it, having base plate, sidewalls and at least one U-shaped side-opening that is rimmed alone with a U-shaped rubber sealing gasket so as to enable a vertical slab gel cassette to join thereat water tightly;
   (ii) said vertical slab gel cassette is for said gel to be cast in it and said electrophoretic separation taking place therein, having two spacer spaced sidewalls, closed left and right edges, a lower opening and a U-notched upper opening;
   (iii) an urging mechanism for forcing said cassette to join said upper buffer chamber at its U-shaped side-opening, so as to form a cassette/upper buffer chamber complex with the U-notched upper opening of said cassette exposing to the inside of said complex;
   (iv) a lower buffer chamber having base plate and sidewalls for housing a volume of lower pH buffer solution, a lower electrode and at least one lower opening of said cassette in it;
   (v) a heat absorbing device for absorbing Joule-heat during an electrophoresis run; and
   (vi) means for preventing the gel from leaking when said gel is cast into said cassette;
   wherein the improved vertical slab gel cassette comprising:
   (a) two panes of un-notched rectangular sidewalls and a pair of flanged spacer strips, each of which has a flat spacer strip part with at least one flanged part connecting it;
   (b) said flat spacer strip parts are clamped between the respective left and right margins of said two sidewalls, while said connected flanged parts rest upon the corresponding edges of said sidewall, so as to form a U-notched upper opening with an even rim for said cassette, due to said flanged parts is as thick as the sidewall it rests upon;
   (c) the flanged parts of said flanged spacer strips not only participate in the formation of said cassette, but also participate in the joining of said cassette to said upper buffer chamber, because said U-shaped rubber sealing gasket rests both upon a portion of a sidewall of said cassette and upon the corresponding flanged parts of said flanged spacer strips when said cassette joins said upper buffer chamber; and
   (d) said flanged spacer strips are affixed on a chosen sidewall, but leaving the other sidewall demountable.

9. The electrophoresis instrument of claim 8, wherein:
   (a) said two panes of rectangular sidewalls comprise a pane of larger sidewall and a pane of smaller sidewall;
   (b) said at least one flanged part is beside the flat spacer strip part;
   (c) said flanged spacer strips are not shorter than said larger side wall; and
   (d) said two flat spacer strip parts are clamped between the respective left and right margins of said two sidewalls, while said two flanged strip parts rest upon the respective left and fight edges of said smaller sidewall.

10. The electrophoresis instrument of claim 9, wherein the further improvement including:
   (a) said pair of flanged spacer strips are linked to each other by a flanged spacer strip beam joined there between the two lower ends thereof, so as to form a U-shaped flanged spacer strip, which has two upward side arms and a horizontal bottom beam portion;
   (b) the flat spacer strip part of said horizontal beam portion has degenerated down into a shark tooth-like tab, which is clamped between the lower margins of said two sidewalls so as to enhance the compressive strength thereof;
   (c) the flanged strip part of said horizontal beam portion has been narrowed down to about 1 to 2 millimeters from its top edge, except the very-left and very-right two tabs, both of which rest upon the bottom edge of said smaller sidewall; and
   (d) said U-shaped flanged spacer strip is affixed on said larger sidewall, but said smaller sidewall is demountable, so as to make the only two assembling seams and the lower opening of said cassette all located on its joining face, hereby enabling said two assembling seams and said lower opening to be sealed-up just by a U-shaped rubber sealing gasket resting upon all three of them simultaneously for gel casting.

11. The electrophoresis instrument of claim 10, wherein said improvement further includes:
   (a) making each U-shaped side opening of said upper buffer chamber to have a coplanar downward lip, and making each said downward lip to have a row of small holes punched along it;
   (b) making said U-shaped rubber sealing gasket to have two horizontal beams at bottom, therefore a flat O-loop is formed at the bottom of this U-shaped rubber sealing gasket;
   (c) said flat O-loop loops around the row of said small hole after said U-shaped rubber sealing gasket mounts onto said upper buffer chamber;
   (d) a strip of wet semipermeable membrane is pasted on the flat O-loop; and
   (e) the lower opening of said cassette is facing the row of said small holes when said cassette is forced to join said upper buffer chamber, hereby said semipermeable membrane is tightly clamped therebetween functionally to seal-up the lower opening of said cassette for gel casting, and hereby allowing subsequently to carry out said electrophoretic separation in said cassette without necessary to move or remove anything.

12. The electrophoresis instrument of claim 8, wherein
   (a) said two panes of rectangular sidewalls comprise a pane of a taller sidewall and a pane of a shorter sidewall;
   (b) said pair of flanged spacer strips each has a flat spacer strip part with a flanged tab part atop it;
   (c) said pair of flanged spacer strips are not shorter than said taller sidewall;
   (d) said two flat spacer strip parts are clamped between the respective left and right margins of said two sidewalls, while said two flanged tab parts rest upon the top edge of said shorter sidewall; and
   (e) said two flanged spacer strips are affixed on said shorter sidewall.

13. The electrophoresis instrument of claim 8, wherein
   (a) said two panes of rectangular sidewalls are identical to each other;
   (b) said pair of flanged spacer strips each has a substantially T-shaped cross section, and is longer than side sidewalls;
   (c) the two flat spacer strip parts of said two flanged spacer strips are clamped between the respective left and right margins of said two sidewalls, while the two T-head parts of said two flanged spacer strips rest upon the respective left and right edges of said two identical sidewalls; and
   (d) said flanged spacer strips are partially protruding above said sidewalls.

14. The electrophoresis instrument of claim 13, wherein said improved vertical slab gel cassette further comprising a V-shaped beak along its upper opening, so as to enable said upper opening to hold a larger volume of sample for the electrophoretic separation.

15. The electrophoresis instrument of claim 8, wherein
   (a) said two panes of rectangular sidewalls comprise a pane of a narrower sidewall and a pane of a wider sidewall;
   (b) said pair of flanged spacer strips each has a flat spacer strip part with a flanged tab part atop it on one face and with a flanged strip part beside it on the other face;
   (c) said pair of flanged spacer strips are longer than said sidewalls;
   (d) said two flat spacer strip parts are clamped between the respective left and right margins of said two sidewalls, while said two atop flanged tab parts rest upon the top edge of said wider sidewall and said two beside flanged strip parts rest upon the respective left and right edges of said narrower sidewall; and
   (e) said pair of flanged spacer strips are affixed on said wider sidewall.

16. The electrophoresis instrument of claim 15, wherein said improved vertical slab gel cassette also comprises a V-shaped beak along its upper opening, so as to enable said upper opening to hold a larger volume of sample for electrophoretic separation.

* * * * *